US005444153A

United States Patent [19]

Goss et al.

[11] Patent Number: 5,444,153
[45] Date of Patent: Aug. 22, 1995

[54] VARIANTS OF PAI-2

[75] Inventors: Neil H. Goss, Wahroonga; Michael A. Richardson, Belrose, both of Australia

[73] Assignee: Biotech Australia Pty Limited, Roseville, Australia

[21] Appl. No.: 768,286

[22] PCT Filed: Dec. 20, 1990

[86] PCT No.: PCT/AU90/00603

§ 371 Date: Oct. 11, 1991

§ 102(e) Date: Oct. 11, 1991

[87] PCT Pub. No.: WO91/09124

PCT Pub. Date: Jun. 27, 1991

[30] Foreign Application Priority Data

Dec. 20, 1989 [AU] Australia .............................. PJ7924

[51] Int. Cl.[6] .......................... C07K 13/00; C12Q 1/00

[52] U.S. Cl. ...................................... 424/141; 424/9.1; 424/145.1; 424/158.1; 435/7.4; 530/388.24; 530/350; 514/12

[58] Field of Search ..................... 424/94.64; 639/226; 514/2

[56] References Cited

FOREIGN PATENT DOCUMENTS 3722673 1/1989 Germany .
WO86/01212 2/1986 WIPO .
8601212 2/1986 WIPO .

(List continued on next page.)

OTHER PUBLICATIONS

Dano et al. (1985) *Advances in Cancer Research* 44:139–266, "Plasminogen Activators, Tissue Degradation, and Cancer".

Ossowski et al. (1983) *Cell* 35:611–619, "Antibodies to Plasminogen Activator Inhibit Human Tumor Metastasis".

Bergman et al. (1986) *Proc. Natl. Acad. Sci. USA* 83:996–1000, "Inhibition of Tumor–Cell–Mediated Extracellular Matrix Destruction by a Fibroblast Proteinase Inhibitor, Protease Nexin I".

Sullivan et al. (1986) *Cell* 45:905–915, "Anticatalytic Monoclonal Antibody to Avian Plasminogen Activator: Its Effect on Behavior of RSV–Transformed Chick Fibroblasts".

Mignatti et al. (1986) *Cell* 47:487–498, "Tumor Invasion Through the Human Amniotic Membrane: Requirement for a Proteinase Cascade".

Ossowski (1988) *Cell* 52:321–328, "Plasminogen Activator Dependent Pathways in the Dissemination of Human Tumor Cells in the Chick Embryo".

Reich et al. (1988) *Cancer Research* 48:3307–3312, "Effects of Inhibitors of Plasminogen Activator, Serine Proteinases, and Collagenase IV on the Invasion of Basement Membranes by Metastatic Cells".

Lack et al. (1958) *Nature* 182:948–949, "Action of Plasmin on Cartilage".

Werb et al. (May 1977) *The New England Journal of Medicine* 296(18):1017–1023, "Endogenous Activation (List continued on next page.)

*Primary Examiner*—Robert A. Wax
*Assistant Examiner*—David B. Schmickel
*Attorney, Agent, or Firm*—Foley & Lardner

[57] ABSTRACT

Variants of the plasminogen activator inhibitor PAI-2 in which the 66-98 amino acid residue region has been altered to eliminate at least one protease sensitive site are provided. The variants of the invention maintain the biological activity of PAI-2 and amino acids up to 65 and from 99 of PAI-2 in frame. The PAI-2 variants of the invention in labelled form, as well as DNA molecules encoding the variants of the invention, transformed host cells expressing the variants of the invention compositions and diagnostic kits comprising the variants of the invention, antibodies against the variants of the invention and processes for the production of the variants, DNA molecules, transformed hosts, compositions and antibodies of the invention are also described.

14 Claims, 13 Drawing Sheets

FOREIGN PATENT DOCUMENTS

WO87/05628  9/1987  WIPO.
0278696  8/1988  WIPO.
WO9103556  3/1991  WIPO.

OTHER PUBLICATIONS of Latent Collagenase by Rheumatoid Synovial Cells".

Mochan et al. (1984) *The Journal of Rheumatology* 11(2):123–128, "Elevations in Synovial Fluid Plasminogen Activator in Patients with Rheumatoid Arthritis".

Kwaan et al. (1969) *Experimental and Molecular Pathology* 11:82–88, "Tissue Repair in Presence of Locally Applied Inhibitors of Fibrinolysis".

Grondahl-Hansen et al. (1988) *The Journal of Investigative Dermatology* 90(6):790–795, "Urokinase- and Tissue-Type Plasminogen Activators in Keratinocytes During Wound Reepithelialization In Vivo."

Sprengers et al. (Feb. 1987) *Blood* 69(2):381–387, "Plasminogen Activator Inhibitors".

Schleuning et al. (1987) *Molecular Cellular Biology* 7(12):4564–4567, "Plasminogen Activator Inhibitor 2: Regulation of Gene Transcription During Phorbol Ester-Mediated Differentiation of U-937 Human Histiocytic".

Antalis et al. (1988) *Proc. Natl. Acad. Sci. USA* 85:985–989, "Cloning and Expression of a cDNA Coding for a Human Monocyte-Derived Plasminogen Activator Inhibitor".

Bunn et al. (1989) *Abstracts of the 2nd International Workshop on the Molecular and Cellular Biology of Plasminogen Activation Brookhaven National Laboratory*, 22, "Expression of Recombinant Human . . .".

Huber et al. (Nov. 1989) *Biochemistry* 28(23):8951–8966, "Implications of the Three-Dimensional Structure of $\alpha_1$-Antitrypsin for Structure and Function of Serpins".

Stephens et al. (Aug. 1985) *Blood* 66(2):333–337, "Minactivin Expression in Human Monocyte and Macrophage Populations".

Richardson et al. (1979) *Brit. J. Cancer* 40:35–43, "Tissue Distribution and Tumor Localization of 99m-Technetium-Labelled Liposomes in Cancer Patients".

Bengent et al. (Oct. 1982) *The Lancet* 739–742, "Liposomally Entrapped Second Antibody Improves Tumor Imaging with Radiolabelled (first) Antitumor Antibody".

Yanisch-Perron et al. (1985) *Gene* 33:103–119, "Improved M13 Phage Cloning Vectors and Host Strains; Nucleotide Sequences of the M13mp18 and pUC19 Vectors".

Coleman et al. (1981) *Methods in Enzymology* 80:408–414, "Coupled Photometric Assay for Plasminogen Activator".

Luckow et al. (Jan. 1988) *Biotechnology* 6:47–55, "Trends in the Development of Baculovirus Expression Vectors".

Kruithof et al. (Aug. 1986) *The Journal of Biological Chemistry* 261(24):11207–11213, "Purification and Characterization of a Plasminogen Activator Inhibitor from the Histiocytic Lymphoma Cell Line U-937".

Andreasen et al. (Jun. 1986) *The Journal of Biological Chemistry* 261(17):7644–7651, "Plasminogen Activator Inhibitor from Human Fibrosarcoma Cells Binds Urokinase-type Plasminogen Activator, But Not Its . . .".

*Molecular Cloning, A Laboratory Manual*, Maniatis et al. (eds), 1st ed. (1982) 153–163, "Technique of Agarose Gel Electrophoresis".

Hanahan (1983) *The Journal of Molecular Biology* 166:557–580, "Studies on Transformation of *Escherichia coli* with Plasmids".

Mott et al. (Jan. 1985) *Proc. Natl. Acad. Sci. USA* 82:88–92, "Maximizing Gene Expression from Plasmid Vectors Containing the $\lambda$ $P_L$ Promoter:" Strategies for Overproducing Transcription Termination Factor $\rho$.

Ho et al. (1989) *Gene* 77:51–59, "Site-Directed Mutagenesis by Overlap Extension Using the Polymerase Chain Reaction".

Haigwood et al. (1989) *Protein Engineering* 2:611–620, "Variants of Human Tissue-type Plasminogen Activator Substituted at the Protease Cleavage Site and Glycosylation Sites, Truncated at the N- . . . ".

Astedt et al. *Journal of Fibrinolysis*, 1:203–208 (1987).

Foon, Cancer Res. vol 49 pp. 1621–1639 Apr. 1989.

Waldmann Science vol. 252 pp. 1657–1662.

Huber et al. Biochemistry vol. 28 (23) pp. 8951–8966, Nov. 14, 1989.

Madison et al. Nature vol. 339 pp. 721–724, Jun. 29, 1989.

FIG. 1A

```
                     GTCAGACAGCAACTCAGAGAATAACCAGAGAACAACCAGATTGAAACA

49  ATG GAG GAT CTT TGT GTG GCA AAC CTC TTT GCC CTC AAT TTA TTC AAG CAT   102
     MET Glu Asp Leu Cys Val Ala Asn Leu Phe Ala Leu Asn Leu Phe Lys His
     1                                                                  18

CTG GCA AAA GCA AGC CCC ACC CAG AAC CTC TTC TCC CCA TGG AGC TCG         156
     Leu Ala Lys Ala Ser Pro Thr Gln Asn Leu Phe Ser Pro Trp Ser Ser
     19   75  ACA Thr                                                    36

ACC ATG GCC ATG GTC TAC ATG CAG CTC TTC TCC AGG GGC AGC AGC ATC         210
     Thr MET Ala MET Val Tyr MET Gln Leu Phe Ser Arg Gly Ser Ser Ile
     37  129 AAC Leu                                                     54

GCC AAG GTG CTT CAG TTT AAT GAA GGA GGC GCC AAT GCA GTT ACC CCC ATG     264
     Ala Lys Val Leu Gln Phe Asn Glu Gly Gly Ala Asn Ala Val Thr Pro MET
     55  183 TCC Ser                                                     72

CCA GAG AAC TTT ACC AGC TGT GGG TTC ATG CAG ATC CAG AAG GGT AGT TAT     318
     Pro Glu Asn Phe Thr Ser Cys Gly Phe MET Gln Ile Gln Lys Gly Ser Tyr
     73  237 GTG Val            291 TTC Phe                              90

CCT GAT GCG ATT TTG CAG GCA CAA GCA GCT GAT AAA ATC CAT TCA TCC TTC CGC 372
     Pro Asp Ala Ile Leu Gln Ala Gln Ala Ala Asp Lys Ile His Ser Ser Phe Arg
     91  345                                                                108
```

FIG. 1B

```
TCT  CTC  AGC  TCT  GCA  ATC  AAT  GCA  399  ACA  GGG  AAT  TAT  TTA  CTG  GAA  AGT  426
Ser  Leu  Ser  Ser  Ala  Ile  Asn  Ala  TCC  Thr  Gly  Asn  Tyr  Leu  Leu  Glu  Ser  GTC
109                                     Ser                                              Val
                                                                                         126

AAT  AAG  CTG  TTT  GGT  GAG  AAG  TCT  453  AGC  TTC  CGG  GAA  TAT  TTA  ATT  CGA  480
Asn  Lys  Leu  Phe  Gly  Glu  Lys  Ser  GCG  Ser  Phe  Arg  Glu  Tyr  Leu  Ile  Arg  CTC
127                                     Ala                                              Leu
                                                                                         144

TGT  CAG  AAA  TAT  TAC  TCC  TCA  GAA  507  CAG  GCA  GTA  GAA  GAC  TTC  CTA  GAA  TGT  534
Cys  Gln  Lys  Tyr  Tyr  Ser  Ser  Glu  CCC  Gln  Ala  Val  Glu  Asp  Phe  Leu  Glu  Cys  GCA
145                                     Pro                                                   Ala
                                                                                              162

GAA  GCT  AGA  AAA  AAG  TCA  AAT  GGT  561  TGG  GTC  AAG  ACT  GAT  CAA  ACC  AAA  588
Glu  Ala  Arg  Lys  Lys  Ser  Asn  Gly  TCC  Trp  Val  Lys  Thr  Asp  Gln  Thr  Lys  AAA
163                                     Ser                                              Lys
                                                                                         180

ATC  CCA  AAC  TTG  CCT  GAA  ATT  AAT  615  GTA  GAT  GGG  ACT  GAT  ACC  ACC  AGG  642
Ile  Pro  Asn  Leu  Pro  Glu  Ile  Asn  TCT  Val  Asp  Gly  Thr  Asp  Thr  Thr  Arg  CTG
181                                     Ser                                              Leu
                                                                                         198

GTG  GCT  GTC  TAC  TTC  AAA  GGA  TGG  669  AAA  ACT  GGG  GAT  CCA  TTT  ATG  AAG  696
Val  Ala  Val  Tyr  Phe  Lys  Gly  Trp  AAG  Lys  Thr  Gly  Asp  Pro  Phe  MET  Lys  CTA
199                                     Lys                                              Leu
                                                                                         216

AAT  GGG  CTT  TAT  CCT  TAT  TTC  CGT  723  TCG  GCT  CAG  CGC  ACA  CCT  GTA  CAG  750
Asn  Gly  Leu  Tyr  Pro  Tyr  Phe  Arg  AAC  Ser  Ala  Gln  Arg  Thr  Pro  Val  Gln  ATG
217                                     Asn                                              MET
                                                                                         234
```

FIG. 1C

| | | | | | | | | | | | | | | | | | | |
|---|---|---|---|---|---|---|---|---|---|---|---|---|---|---|---|---|---|---|
| ATG MET 235 | TAC Tyr | TTG Leu | CGT Arg | GAA Glu | AAG Lys | CTA Leu | AAC Asn | 777 ATT Ile | GGA Gly | TAC Tyr | ATA Ile | GAA Glu | GAC Asp | CTA Leu | AAG Lys | GCT Ala | 804 CAG Gln 252 |
| ATT Ile 253 | CTA Leu | GAA Glu | CTC Leu | CCA Pro | TAT Tyr | GCT Ala | GGA Gly | 831 GAT Asp | GTT Val | AGC Ser | ATG MET | TTC Phe | TTG Leu | TTG Leu | CTT Leu | CCA Pro | 858 GAT Asp 270 |
| GAA Glu 271 | ATT Ile | GCC Ala | GAT Asp | GTG Val | TCC Ser | ACT Thr | GGC Gly | 885 TTG Leu | GAG Glu | CTG Leu | CTG Leu | GAA Glu | AGT Ser | GAA Glu | ATA Ile | ACC Thr | 912 TAT Tyr 288 |
| GAC Asp 289 | AAA Lys | CTC Leu | AAC Asn | AAG Lys | TGG Trp | ACC Thr | AGC Ser | 939 AAA Lys | GAC Asp | AAA Lys | ATG MET | GCT Ala | GAA Glu | GAT Asp | GAA Glu | GTT Val | 966 GAG Glu 306 |
| GTA Val 307 | TAC Tyr | ATA Ile | CCC Pro | CAG Gln | TTC Phe | AAA Lys | TTA Leu | 993 GAA Glu | GAG Glu | CAT His | TAT Tyr | GAA Glu | GAT Asp | AGA Arg | TCC Ser | ATT Ile | 1020 CTG Leu 324 |
| AGA Arg 325 | AGC Ser | ATG MET | GGC Gly | ATG MET | GAG Glu | GAC Asp | GCC Ala | 1047 TTC Phe | AAC Asn | AAG Lys | GGA Gly | CGG Arg | GCC Ala | AAT Asn | TTC Phe | TCA Ser | 1074 GGG Gly 342 |
| ATG MET 343 | TCG Ser | GAG Glu | AGG Arg | AAT Asn | GAC Asp | CTG Leu | TTT Phe | 1101 CTT Leu | TCT Ser | GAA Glu | GTG Val | TTC Phe | CAC His | CAA Gln | GCC Ala | ATG MET | 1128 GTG Val 360 |

FIG. 1D

| | | | | | | | | | 1155 | | | | | | | 1182 |
|---|---|---|---|---|---|---|---|---|---|---|---|---|---|---|---|---|
| GAT | GTG | AAT | GAG | GGC | ACT | GAA | GCA | GCC | GCT | GGC | ACA | GGA | GGT | GTT | ATG | ACA |
| Asp | Val | Asn | Glu | Gly | Thr | Glu | Ala | Ala | Ala | Gly | Thr | Gly | Gly | Val | MET | Thr |
| 361 | | | | | | | | | | | | | | | | 378 |

| | | | | | | 1209 | | | | | | | | | | 1236 |
|---|---|---|---|---|---|---|---|---|---|---|---|---|---|---|---|---|
| GGG | AGA | ACT | GGA | CAT | GGA | CAG | TTT | GTG | GCA | GAT | CAT | CCT | TTT | CTT | TTT |
| Gly | Arg | Thr | Gly | His | Gly | Gln | Phe | Val | Ala | Asp | His | Pro | Phe | Leu | Phe |
| 379 | | | | | | | | | | | | | | | | 396 |

| | | | | | | 1263 | | | | | | | | | | 1290 |
|---|---|---|---|---|---|---|---|---|---|---|---|---|---|---|---|---|
| CTT | ATT | ATG | CAT | AAG | ATA | ACC | AAC | TGC | ATT | TTA | TTT | TTC | GGC | AGA | TTT | TCC |
| Leu | Ile | MET | His | Lys | Ile | Thr | Asn | Cys | Ile | Leu | Phe | Phe | Gly | Arg | Phe | Ser |
| 397 | | | | | | | | | | | | | | | | 414 |

CCC TAA AACTAAGCGTGCTGCTTCTGCAAAGATTTTGTAGATGAGCTGTGTGCCTCAGAATTGCTAT
Pro *
415
                                                                                1359

1430
TTCAAATTGCCAAAATTTAGAGATGTTTTCTACATATTTCTGCTCTTCTGAACAACTTCTGCTACCCACT

1501
AAATAAAAACACAGAAATAATTAGACAATTGTCTATTATAACATGACAACCCTATTAATCATTGGTCTTC

1572
TAAAATGGGATCATGCCCATTTAGATTTCCTTACTATCAGTTTATTTTATAACATTAACTTTTACTTTG

1610
TTATTTATTATTTTATATAATGGTGAGTTTTAAATTA

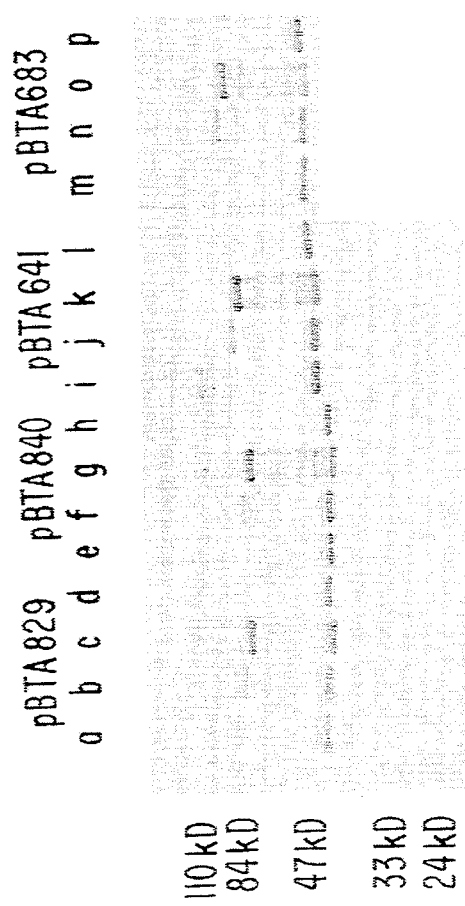

FIG. 4

NATIVE PAI-2

```
    241
     |
    CCC AAT GCA GTT ACC CCC ATG ACT CCA GAG AAC TTT ACC AGC TGT GGG TTC ATG
    Ala Asn Ala Val Thr Pro Met Thr Pro Glu Asn Phe Thr Ser Cys Gly Phe Met
    65                                                                    82

295                                                              346
     |                                                                |
    CAG CAG ATC CAG AAG GGT AGT TAT CCT GAT GCG ATT TTG CAG GCA CAA GCT GCA   (SEQ ID No. 3)
    Gln Gln Ile Gln Lys Gly Ser Tyr Pro Asp Ala Ile Leu Gln Ala Gln Ala Ala
    83                                                                   100
```

Δ 74-96 PAI-2

```
    241                                 265    337
     |                                   |      |
    CCC AAT GCA GTT ACC CCC ATG ACT  CCA GCA CAA GCT GCA   (SEQ ID No. 5)
    Ala Asn Ala Val Thr Pro Met Thr  Pro Ala Gln Ala Ala
    65                           73   97              100
```

Δ 66-98 PAI-2

```
    241  343  346
     |    |    |
    GCC GCT GCA
    Ala Ala Ala
    65   99  100
```

FIG. 5

OLIGO A₁ (18 MER) — ADAPTOR FOR REPLACING HinfI/PstI REGION OF PAI-2 GENE

5' - ACT CCA GCA CAA GCT GCA - 3'

OLIGO A₂ (11 MER) — COMPLEMENTARY TO A₁

5' - GCT TGT GCT GG - 3'

OLIGOS A₁/A₂ — AFTER KINASING, MIXING AND ANNEALING

```
HinfI                  PstI
CO-HESIVE END          CO-HESIVE END

5' - ACT CCA GCA CAA GCT GCA - 3'   (SEQ ID NO. 7)
3' -     GGT CGT GTT CG     - 5'   (SEQ ID NO. 8)
         Thr Pro Ala Gln Ala Ala   - ENCODED AMINO ACIDS
          72  73  97  98  99 100   - POSITION IN NATIVE PAI-2 PROTEIN
```

FIG. 7A

|          | a | b   | c   | d   | e   | f   | g   | h |          |
|----------|---|-----|-----|-----|-----|-----|-----|---|----------|
| plasmid  | - | 641 | 641 | 829 | 829 | 836 | 836 | - |          |
| u-pa     | + | -   | +   | -   | +   | -   | +   | - |          |

|          | a | b   | c   | d   | e   | f   | g   | h |          |
|----------|---|-----|-----|-----|-----|-----|-----|---|----------|
| plasmid  | - | 641 | 641 | 829 | 829 | 836 | 836 | - |          |
| u-pa     | + | -   | +   | -   | +   | -   | +   | - |          |

A134/301 (22mer) — oligo for PCR reaction, noncoding strand

```
           541                      520
            |                        |
5'- CTT CTT CTG CAG ATT CTA GGA A -3'   (SEQ ID NO. 9)
```

A134/304 (29mer) — oligo for PCR reaction, noncoding strand

```
        351   343 243              224
         |     |   |                |
5'- AT CTG CAG CGG CTC CCA CTT CAT TAA ACT -3'   (SEQ ID NO. 10)
```

A134/305 (28mer) — oligo for PCR reaction, coding strand

```
    235  243 343                      361
     |    |   |                        |
5'- GTG GGA GCC GCT GCA GAT AAA ATC CAT T -3'   (SEQ ID NO. 11)
```

S3  S4
(NON REDUCED)

S4  S4
(NON  (REDUCED)
REDUCED)

VARIANTS OF PAI-2

TECHNICAL FIELD

This invention relates to genetically engineered variants of a plasminogen activator inhibitor, PAI-2.

DEPOSITION OF MICROORGANISMS

*E. coli* strain BTA 1445 was deposited with the American Type Culture Collection of 12301 Parklawn Drive, Rockville Md. 20852, U.S.A. in accordance with the provisions of the Budapest Treaty under accession number ATCC 53585 on Feb. 11, 1987.

BACKGROUND ART

Plasminogen activators (PAs) are serine proteases which convert the abundant extracellular zymogen, plasminogen, into plasmin, an active protease which can promote degradation of all components of the extracellular matrix. (Dano et al. Adv. Cancer Res. 44: 139–266, 1985).

Two different types of PAs have been recognised in mammalian tissues:

(1) Tissue-type Plasminogen Activator (t-PA). t-PA is a serine protease with a molecular weight of about 70,000, composed of one polypeptide chain containing 527 amino acids. Upon limited digestion with plasmin the molecule is converted to a two-chain activator linked by one disulphide bond. This occurs by cleavage of the Arg 275 - Ile 276 peptide bond yielding a heavy chain ($M_r$ 38,000) derived from the N-terminal part of the molecule and a light chain ($M_r$ 32,000) comprising the COOH-terminal region. The catalytic site located in the light chain of t-PA is composed of His 322, Asp 371 and Ser 478. t-PA specifically catalyses the hydrolysis of an Arg 560 - Val 561 bond in plasminogen. Fibrin has been found to strongly stimulate plasminogen activation by t-PA.

(ii) Urokinase-type Plasminogen Activator (U-PA). u-PA has an $M_r$ of 50,000 and occurs in a one-polypeptide and a two polypeptide chain form. The one chain form is an inactive proenzyme, while the two-chain form is the active enzyme. u-PA has a substantial plasminogen activator activity in the absence of fibrin and is not stimulated by its presence. t-PA's high affinity for fibrin suggests that it is mostly associated with a fibrinolytic function while u-PA is associated with extracellular proteolytic events such as tissue remodelling and destruction (i.e. organ involution, inflammatory reactions and particularly in the invasive growth and metastatic spread of malignant tumours).

Experimental use of t-PA and single chain u-PA as thrombolytic agents in man has been promising. However, it has become apparent that PAs may have a less pronounced fibrin specificity in man than was anticipated from several animal models, suggesting a need for further improvement either of the agents or of their administrative schemes in clinical thrombolytic therapy. One possibility is the use of specific fast-acting protein inhibitors of PAs to modulate the systemic fibrinolytic effects of PAs.

Recent evidence suggests that urokinase-mediated plasminogen activation may also play a role in the invasive behaviour of malignant cells. With few exceptions malignant cells release PAs in abnormally high amounts. Ossowski and Reich (Cell 35: 611–619, 1983) reported that anti-urokinase antibodies inhibited the metastasis of human epidermoid carcinoma cells seeded onto chick embryo chorioallantoic membranes. Bergman et al (Proc. Natl. Acad. Sci. 83: 996–1000, 1986) have shown that protease nexin I, a fibroblast-secreted inhibitor of urokinase and plasmin, effectively inhibits the cell mediated degradation of extracellular matrix (ECM) by human fibrosarcoma (HT1080) cells. Finally, Sullivan and Quigley (Cell 45: 905–915, 1986) have demonstrated that a monoclonal antibody to PA inhibits the degradation of ECM by Rous sarcoma virus-transformed chick fibroblasts. It follows from these observations and those of others [e.g. Mignatti et al., Cell 47: 487 (1986); Ossowski, Cell 52: 321 (1988); Reich et al, Cancer Res. 48: 3307 (1988)] that specific protease inhibitors of urokinase may play a critical role in altering the levels of active tumour cell PA in tumour tissue and therefore influence tumour growth and invasion in vivo.

There are other indications that a specific inhibitor of urokinase-type plasminogen activator has a role in modern medicine. PAs are involved in a range of inflammatory conditions such as arthritis. Plasmin can degrade cartilage [Lack, CH & Rogers, HJ (1958) Nature 182: 948] and low levels of fibrinolytic activity due to plasmin have been detected histochemically in synovial membranes. The PA/plasmin system has been detected in rheumatoid cell cultures [Werb, Z et al. (1977) New Engl J Med 296, 1017] and elevated levels of uPA have been noted in rheumatoid synovial fluid [Mochan, E. & Uhl, J. (1984) J. Rheumatol 11, 123]. Hence, the use of a specific inhibitor of uPA in arthritis could reverse the tissue destruction associated with this disease.

Other conditions where the application of a specific PA inhibitor may be of use include diseases or conditions such as osteoarthritis, multiple sclerosis, colitis ulcerosa, SLE-like disease, psoriasis, pemphigus, corneal ulcer, gastroduodenal ulcer, purpura, periodontitis, haemorrhage and muscular dystrophy. Finally, a PA inhibitor could have a significant role in skin wound healing and tissue repair especially since two trypsin inhibitors have been shown to enhance formation of connective tissue with increased tensile strength of the wound tissue [Kwaan, HC and Astrup, T (1969) Exp. Molec. Path. 11, 82] and keratinocytes are known to produce both uPA and tPA [Grondahl-Hansen, J et al. (1988) J. Invest Dermatol].

PA inhibitors, members of the serpin gene family (Sprengers and Kluft, Blood 69: 381–387, 1987), have been classified into four immunologically different groups:

1) Endothelial cell type inhibitor, PAI-1.
2) Placental type PA-inhibitor, PAI-2.
3) Urinary type PA-inhibitor, PAI-3.
4) Protease Nexin I, PNI.

PAI-2 ($M_r$ about 46,000) has been purified from placental tissue, monocytes and the human monocytic cell line U937. The PAI-2 inhibitors from these different sources are immunologically related and recent cDNA sequence analyses of PAI-2 derived from human placenta and the human U937 cell line confirmed they are identical, although two forms of the molecule exist differing in only 3 single amino acid residues. Both cDNA forms have been isolated from U937 cells. (Schleuning et al. Mol. Cell. Biol. 7: 4564–4567, 1987; Antalis et al. Proc. Natl. Acad. Sci. 85: 985–989, 1988). PAI-2 reacts with both u-PA and t-PA (better with two chain t-PA than with single chain t-PA) to form SDS stable complexes. PAI-2 does not bind to fibrin or to fibrin-bound t-PA.

As is the case with most potent biologically active proteins, PAI-2 is produced in very small amounts in vivo and as such is difficult to purify and characterise by conventional biochemical approaches. The recent expression of PAI-2 in bacterial cells (Antalis et al. Proc. Natl. Acad. Sci. 85: 985–989, 1988; Bunn et al, Abstracts of the Second International Workshop on the Molec. and Cell. Biol. of Plasminogen Activation, Brookhaven National Lab., April 1989), now allows the production of quantities of purified PAI-2 needed to evaluate its biological efficacy in the various potential clinical applications described above.

DISCLOSURE OF THE INVENTION

Knowledge of the complete nucleotide sequence of PAI-2 allows specific genetic manipulations to be made which produce variants of PAI-2 which may exhibit improved properties compared with the native molecule.

Desirable improved properties include increased in vivo half life, increased or altered specificity, and/or improved pharmaceutical effectiveness.

The alterations may provide different properties which open up new areas of application or variants which are more amenable to industrial production, thus leading to improved production processes.

A unique difference between PAI-2 and the other serpins is the additional stretch of 33 residues (66–98) in the $C_1$-D interhelical region [Huber, R and Carrell RW (1989) Biochemistry 28 8951–8966]. This region is generally either limited to a short 9-residue stretch, as in ovalbumin or is absent, as in other members of the superfamily (e.g. human $\alpha$1-antitrypsin, human antithrombin III). The significance of this structure is unknown. The present inventors have discovered that this region is sensitive to proteases, leading to the generation of a 37 kD form of PAI-2 during production. The presence of a 37 kD contaminant in PAI-2 preparations is not likely to be acceptable to regulatory authorities. Further, the 37 kD form of PAI-2 is unable to bind to U-PA.

Thus it is desirable to provide biologically active PAI-2 molecules which are not sensitive to protease. When providing a variant of a particular protein which lacks an undesirable characteristic, it is not possible to predict whether the variant will maintain the desired biological activity of the parent protein, particularly where the alterations are significant. Given that the 66–98 amino acid region of PAI-2 is unique to PAI-2 it would be anticipated that alterations to this region of the molecule would be likely to render the resultant molecule inactive or at least have an adverse effect on its activity. Surprisingly, the variants of the present invention do retain the biological activity of native PAI-2, whilst lacking protease sensitivity.

Changes to PAI-2, can be made by modifying individual amino acids of PAI-2 by site-directed mutagenesis of the DNA or by wholesale restructuring by DNA deletion or insertion to provide variants of the invention. The actual manipulations of the DNA can in general be performed in accordance with standard techniques in the art. The specific changes exemplified are produced by restructuring by DNA deletion.

According to a first embodiment of this invention there is provided a PAI-2 variant in which the 66–98 amino acid residue region of PAI-2 has been altered to eliminate at least one protease sensitive site which variant maintains biological activity of PAI-2 and amino acids to 65 and from 99 of PAI-2 in frame. Preferably the variant is a deletion variant.

The invention particularly provides the PAI-2 variant Δ66–98 as herein defined wherein Δ66–98 has amino acids 66–98 inclusive of the PAI-2 amino acid sequence (SEQ ID NO: 1) deleted. The invention also particularly provides the variant Δ74–96 as herein defined, wherein Δ74–96 has amino acids 74–96 inclusive of the PAI-2 amino acid sequence deleted.

According to a second embodiment of this invention, there is provided a PAI-2 variant of the first embodiment in labelled form.

According to a third embodiment of this invention there is provided a DNA molecule, the sequence of which encodes a PAI-2 variant of the first embodiment.

According to a fourth embodiment of this invention there is provided a recombinant DNA molecule comprising a DNA molecule of the third embodiment, and vector DNA.

Typically, the vector DNA is plasmid DNA.

Preferred plasmid vectors of the invention include E. coli expression vectors such as those based on the $P_L$ promoter, lac promoter, tac promoter or trp promoter, pGEM4Z and vectors derived therefrom, pSp70 and vectors derived therefrom, baculovirus transfer vectors such as pac373, pac360 and vectors derived therefrom, mammalian expression vectors such as pBPV-1, pBPV-BV1, pdBPV-MMTneo, SV40 based expression vectors such as pBTA613, and vectors derived therefrom, vaccinia virus expression vectors, retroviral expression vectors and other vectors used for the expression of recombinant DNA molecules in homologous or heterologous hosts.

Vectors derived from these vectors are those vectors obtained by making structural alterations to these vectors. Examples of the types of alteration include those made for the purpose of increasing expression from a particular vector.

pBTA613 is a mammalian cell expression vector. Foreign genes are expressed by cloning into the multiple cloning site flanked upstream by the SV40 early promoter and downstream by SV40 polyadenylation signals. pBTA613 comprises the following fragments in order. The 345bp PvuII-HindIII fragment from the SV40 origin, 51bp HindIII-EcoRI multiple cloning sites from pUC18, 75bp EcoRI-AatII fragment from pBR327, 853bp BamHI-XhoI fragment from pMSG with AatII linkers attached to both ends, 2262bp AatII-EagI fragment from pBR327, 27bp oligonucleotide (GGCCCATATGATATCTCGAGACTAGTC: SEQ ID NO: 4), 288bp EagI-SalI fragment from pBR327, 345bp PvuII-HindIII fragment from the SV40 origin, 734bp HindIII-BglII fragment encoding mouse dihydrofolate reductase from pSV2-DHFR, 141bp Sau3A fragment from SV40 small t intron region and 293bp Sau3A fragment from SV40 early polyadenylation region. The HindIII site at the 5' end of the dhfr gene was deleted using S1 nuclease, other incompatible ends were made flush using S1 nuclease or filled in with dNTPs and DNA polymerase I (Klenow).

Preferred recombinant DNA molecules of the invention include pBTA829, pBTA840, pMINDEL 74–96, and derivatives of these recombinant DNA molecules.

Derivatives of these recombinant DNA molecules are molecules derived from these molecules and include molecules where alterations have been made to the DNA structure for purposes such as improving or altering the control of expression of the encoded PAI-2 variant. The recombinant DNA molecule derivatives of the invention maintain the PAI-2 variant coding region of the parent molecule.

According to a fifth embodiment of this invention there is provided a transformed host cell transformed by a recombinant DNA molecule of the fourth embodiment.

Typically, host cell lines are derived from suitable *E. coli* K-12 strains. They can also be derived from eukaryotic organisms, and can include COS cells, CHO cells, U937 cells, BHK-21 cells, Vero cells, CV1 cells, C127 cells and cell lines derived from the insects *Spodoptera frugiperda* and *Bombyx mori*.

According to a sixth embodiment of this invention there is provided a process for producing a PAI-2 variant of the first embodiment, which process comprises: deleting nucleotides from the 66–98 amino acid residue region of a DNA molecule encoding PAI-2 such that the amino acids up to 65 and from 99 remain in frame and the resulting variant maintains the biological activity of PAI-2.

According to a seventh embodiment of this invention there is provided a process for producing a recombinant DNA molecule of the fourth embodiment, which process comprises inserting a DNA molecule of the third embodiment into vector DNA.

According to an eighth embodiment of this invention there is provided a process for producing a transformed host cell of the fifth embodiment, which process comprises making a suitable host cell competent for transformation, and transforming the competent host cell with a recombinant DNA molecule of the fourth embodiment.

According to a ninth embodiment of this invention there is provided a therapeutic and/or a diagnostic composition comprising an effective amount of at least one PAI-2 variant of the first embodiment together with a pharmaceutically acceptable carrier, excipient and/or diluent. The pharmaceutically acceptable carriers, diluents and excipients which may be used can be selected from those standardly used in the preparation of pharmaceutical formulations. When used for diagnostic purposes the agent may comprise the at least one variant in labelled form. PAI-2 variants may be labelled with a radioisotope such as $I^{131}$ or conjugated to an appropriate enzyme or other chemical agent. Particularly provided are such agents wherein the at least one variant comprises $\Delta 66$–98 and/or $\Delta 74$–96, as herein defined. When used for the production of antibodies the composition may comprise an adjuvant.

According to a tenth embodiment of this invention there is provided a method of inhibiting tumour invasion and/or treating tumours comprising administering to a patient requiring such treatment a therapeutically effective amount of a PAI-2 variant of the first embodiment and/or a composition of the ninth embodiment.

According to an eleventh embodiment of this invention there is provided a method of treatment of an inflammatory disease such as rheumatoid arthritis, osteoarthritis, inflammatory bowel disease, ulcerative colitis, psoriasis or pemphigus comprising administering to a patient requiring such treatment a therapeutically effective amount of a PAI-2 variant of the first embodiment and/or a composition of the ninth embodiment.

According to a twelfth embodiment of this invention there is provided a method of treatment of a fibrinolytic disorder, such as systemic fibrinolysis, comprising administering to a patient requiring such treatment a therapeutically effective amount of a PAI-2 variant of the first embodiment and/or a composition of the ninth embodiment.

According to a thirteenth embodiment of this invention there is provided a method of treatment of a condition such as multiple sclerosis, corneal or gastroduodenal ulceration, purpura, periodontitis, haemorrhage or muscular dystrophy, comprising administering to a patient requiring such treatment a therapeutically effective amount of a PAI-2 variant of the first embodiment and/or a composition of the ninth embodiment.

According to a fourteenth embodiment of this invention there is provided a method for locating and/or defining the boundaries of a tumour in a histological specimen or in vivo which method comprises applying an effective amount of a labelled PAI-2 variant of the second embodiment to the specimen or administering it to a host in need of in vivo imaging and determining by imaging, location of concentration of the label.

According to a fifteenth embodiment of this invention there is provided a method of improving the clinical efficacy of PA treatment of thrombosis which method comprises administering a therapeutically effective amount of a PAI-2 variant of the first embodiment and/or a composition of the ninth embodiment to a host in need of such treatment to counteract systemic activation of fibrinolysis and concomitant fibrin/fibrinogen breakdown.

According to a sixteenth embodiment of this invention there is provided an antibody against a PAI-2 variant of the first embodiment. The antibody may be either a monoclonal or a polyclonal antibody.

The antibodies of the present invention can be used for detecting PAI-2 and hence should be useful in the detection or monitoring of a number of disease states or conditions such as monocytic leukaemia, cancer, foetal development and chronic inflammatory diseases.

According to a seventeenth embodiment of this invention there is provided a process for preparing an antibody of the sixteenth embodiment, which process comprises immunizing an immunocompetent host with an effective amount of a PAI-2 variant of the first embodiment and/or a composition of the ninth embodiment.

According to an eighteenth embodiment of this invention there is provided an antibody composition comprising an antibody of the sixteenth embodiment together with a pharmaceutically acceptable carrier, diluent and/or excipient.

The antibody composition of the invention is of use in the detection or monitoring of disease states or conditions for which the antibodies of the sixteenth embodiment can be used.

According to a nineteenth embodiment of this invention, there is provided a diagnostic reagent comprising an antibody of the sixteenth embodiment and/or an antibody composition of the eighteenth embodiment.

According to a twentieth embodiment of this invention there is provided a conjugate comprising a variant of the first embodiment linked to a cytotoxin. Examples of cytotoxins which may be used in the preparation of conjugates of the invention include: abrin; ricin; mellitin; gelonin; and the A sub unit from Diphtheria, tetanus, clostridial, Pertussis, Shigella, Pseudomonas, cholera or *E. coli* labile toxin.

Previous studies have demonstrated that human colon cancers produce significantly greater amount of urokinase-type plasminogen activator than that occurring in adjacent non-involved tissue. PAI-2 has been found to be capable of binding to and inhibiting this tumour associated plasminogen activator (Stephens et al. *Blood* 66 333–337, 1985). Thus, it follows that biologically active PAI-2 variants have application as reagents for identifying and defining tumours both in vivo and in histological specimens. For imaging tumours in vivo PAI-2 variants of the invention may be labelled with an appropriate isotope, such as Technetium-99m (Richardson, V. J. Brit. J. Cancer 40; 35, 1979) or Iodine-131 (Begent, R. H. J. Lancet, Oct. 2, 1982). Following administration of the PAI-2 variant preparation, the location and boundaries of the tumour may be determined by known radioisotopic methods, such as gamma-camera imaging. Thus, PAI-2 variants offer a sensitive method for enabling the identification of small metastic cancers particularly those arising after surgical intervention. In the analysis of histochemical specimens, PAI-2 variants or antibodies raised thereto, may be labelled with an isotope such as $I^{131}$ or conjugated to an appropriate enzyme or other chemical reagent. On contact with a histological specimen, such as a biopsy section, a PAI-2 variant of the invention will bind to the tumour type plasminogen activator at its place of secretion, thereby identifying the tumour boundaries and potentially the metastatic state of the tumour. In addition to diagnostic applications, PAI-2 variants are also indicated for use in the direct treatment of tumours. As specific inhibitors of the enzyme implicated in the process by which tumors invade surrounding tissues (Dano, K. et al., Adv. in Cancer Res. 44, 139, 1985), regulation and in particular, inhibition of tumour growth and metastases can be achieved. Furthermore, PAI-2 variants can be used as a drug delivery system to deliver lectins or toxins directly to growing tumours. It will be appreciated that this system could offer many advantages in terms of specificity and extremely potent tumouricidal capability.

Other biological processes in which urokinase-type plasminogen activators have been implicated involve those physiological events associated with invasion and tissue destruction, such as chronic inflammatory conditions including rheumatoid arthritis. PAI-2 variants are indicated to have a therapeutic effect when administered in vivo in ameliorating such conditions.

According to a twenty-first embodiment of this invention there is provided a cytotoxic composition comprising a conjugate of the twentieth embodiment together with a pharmaceutically acceptable carrier, diluent and/or excipient.

According to a twenty-second embodiment of this invention, there is provided a method of delivering a cytotoxic agent to a tumour which method comprises administering an effective amount of a conjugate of the twentieth embodiment, and/or a cytotoxic composition of the twenty-first embodiment to a host in need of such treatment.

According to a twenty-third embodiment of this invention there is provided a diagnostic kit comprising a variant of the first embodiment and/or a composition of the ninth embodiment as a standard and an antibody of the sixteenth embodiment, an antibody composition of the eighteenth embodiment and/or a diagnostic reagent of the nineteenth embodiment.

The diagnostic kits of the invention are of use in the detection or monitoring of diseases and conditions for which the antibodies of the invention can be used.

BRIEF DESCRIPTION OF THE DRAWINGS

FIG. 1 PAI-2 cDNA and amino acid sequence (SEQ ID NO: 1). The arrows indicate the specific cleavage points so far identified.

FIG. 3 Schematic representation of PAI-2 specific bands detected in a binding experiment with U-PA, two chain t-PA and single chain t-PA.

FIG. 4 Specific nucleotide and amino acid changes within PAI-2 to create the deletion variants Δ66–98 (SEQ ID NO: 5) and Δ74–96 (SEQ ID NO: 3). The altered regions are described in: bases 214–222 of SEQ ID NO: 5 and amino acid residues 65–67 of SEQ ID NO: 6 for 66–98; bases 214–252 of SEQ ID NO: 3 and amino acid residues 65–77 of SEQ ID NO: 4 for 74–96; and compared with the native sequence in bases 241–348 of SEQ ID NO: 1 and amino acid residues 65–100 of SEQ ID NO: 2.

FIG. 5 Sequence of oligonucleotides A1 (SEQ ID NO: 7)and A2 (SEQ ID NO: 10), used to create the deletion variant Δ74–96 in pBTA829.

FIG. 7 Schematic representation of PAI-2 specific bands (FIG. 7A) and urokinase specific bands (FIG. 7B) detected in a u-PA binding experiment.

FIG. 8 Sequence of oligonucleotides A134/301 (SEQ ID NO: 11), A134/304 (SEQ ID NO: 12) and A134/305 (SEQ ID NO: 11), used to create the deletion variant Δ66–98 in pBTA840. The location of the oligonucleotides within the PAI-2 coding region is indicated by the accompanying numbers. The numbering of the bases is as in FIG. 1.

Oligos A134/301 and A134/305 were used in a PCR reaction to generate a DNA fragment spanning the PAI-2 coding region from bases 235 to 541, with bases 244 to 342 inclusive deleted. Oligos A134/304 and the Sp6 sequencing primer were used in a PCR reaction to generate a DNA fragment spanning the PAI-2 coding region from bases 49 to 351, with bases 244 to 342 inclusive deleted. Oligos A134/301 and the Sp6 sequencing primer were used in a PCR reaction containing the products of the above two PCR reactions to generate a DNA fragment spanning the PAI-2 coding region from bases 49 to 541, with bases 244 to 342 inclusive deleted.

Figure 9:
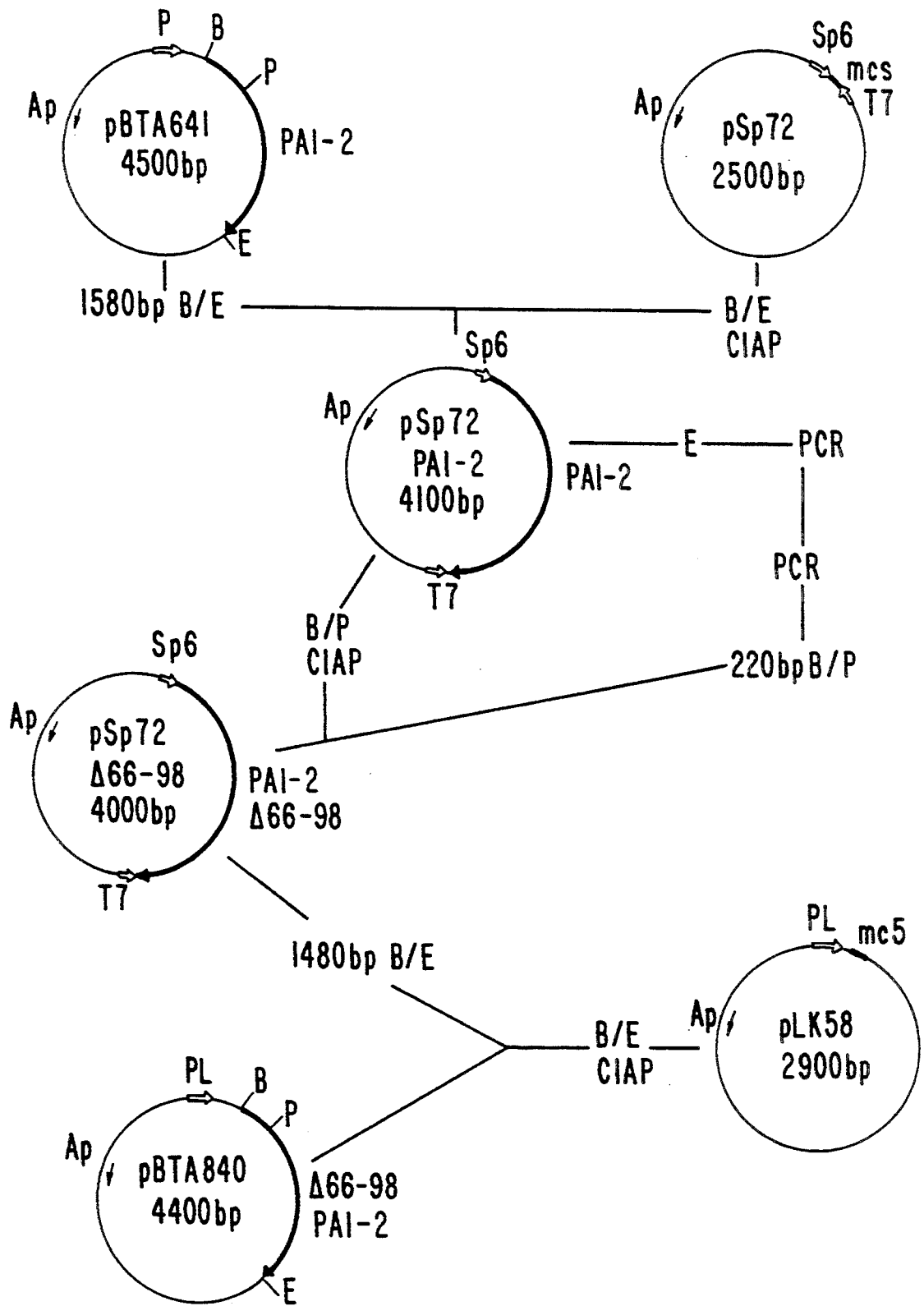

FIG. 9 Construction of plasmid pBTA840 containing the deletion variant, Δ66–98. (Abbreviations used: B, Bgl II; E, EcoRI; P, Pst I; $P_L$, leftwards promoter of bacteriophage lambda; Sp6, promoter from bacteriophage Sp6; $T_7$, promoter from bacteriophage $T_7$; Ap, ampicillin resistance gene; CIAP, calf intestine alkaline phosphatase; PCR, polymerase chain reaction).

Figure 10A:
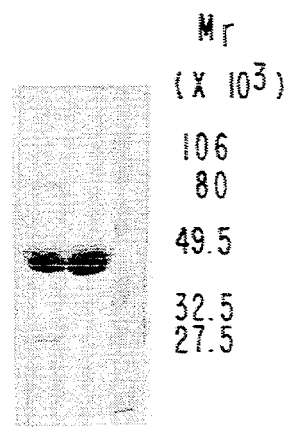
Figure 10B:
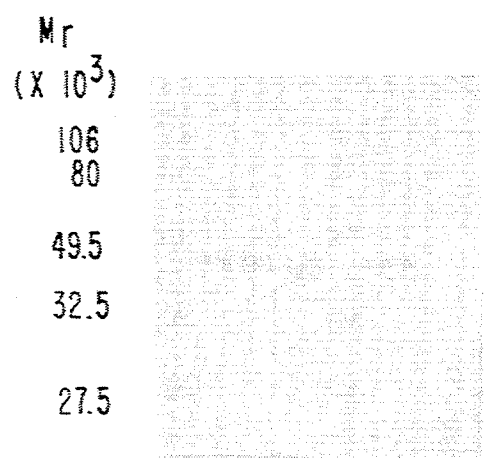

FIG. 10 SDS-PAGE analysis of purified PAI-2 Δ66–98. 12% polyacrylamide gel (a.) and western (b.) (Anti-PAI-2 polyclonal antibodies) of the PAI-2 deletion mutant 66–98.

BEST MODE FOR CARRYING OUT THE INVENTION

The recombinant DNA molecules and transformed hosts of the invention are prepared using standard techniques of molecular biology.

Variants of the invention are obtained by culturing the transformed hosts of the invention under standard conditions as appropriate to the particular host and separating the variant from the culture by standard techniques. The variants may be used in impure form or may be purified.

Changes to PAI-2 can be made by modifying individual amino acids of PAI-2 by site-directed mutagenesis of the DNA or by wholesale restructuring by DNA deletion or insertion. These changes can be accomplished in a variety of ways well known to those skilled in the art [e.g. "Molecular Cloning, A Laboratory Manual" Chapter 15 "Site-directed Mutagenesis of cloned DNA" J. Sambrook, E. F. Fritsch, T. Maniatis (eds) 1989; "Current Protocols in Molecular Biology" Chapter 8 "Mutagenesis of Cloned DNA" Ausubel, Brent, Kingston, Moore, Seidman, Smith and Struhl (eds) 1989], and include the use of oligonucleotides for point insertion and deletion mutagenesis, degenerate oligonucleotides for nested mutations, the combing of long oligonucleotides to create a gene or gene segment with any desired changes, the use of Bal 31, DNAase I or Exonuclease III to create deletion mutants, the use of chemicals and the use of polymerase chain reaction (PCR). These techniques can be used to alter the 66–98 amino acid residue region of the PAI-2 molecule to produce PAI-2 variants. The PAI-2 variants produced can then be screened by the techniques described in Examples 1 and 2 to determine whether particular variants lack the protease sensitivity of PAI-2 in the 66–98 amino acid residue region as evidenced by the absence of the 37 kD form and tested for maintenance of biological activity of PAI-2 as described in Examples 1 and 2 for Δ66–98 and Δ74–96.

The compositions of the invention are prepared by mixing, preferably homogeneously mixing, variant with a pharmaceutically acceptable carrier, diluent, and/or excipient using standard methods of pharmaceutical preparation.

The amount of variant required to produce a single dosage form will vary depending upon the condition to be treated, host to be treated and the particular mode of administration. The specific dose level for any particular patient will depend upon a variety of factors including the activity of the variant employed, the age, body weight, general health, sex, and diet of the patient, time of administration, route of administration, rate of excretion, drug combination and the severity of the condition undergoing treatment. The amounts required may be determined in accordance with standard pharmaceutical techniques.

The composition may be administered parenterally in unit dosage formulations containing conventional, non-toxic, pharmaceutically acceptable carriers, diluents and/or excipients as desired.

Injectable preparations of the variants of the invention, for example, sterile injectable aqueous or oleaginous suspensions may be formulated according to the known arts using suitable dispersing or wetting agents and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

It is anticipated that it may be possible to deliver the variants of the invention orally or topically as appropriate delivery systems are developed.

Antibodies are raised using standard vaccination regimes in appropriate hosts. The host is vaccinated with a variant or composition of the invention. The compositions used for vaccination purposes may include an adjuvant.

Suitable adjuvants for the vaccination of animals include but are not limited to oil emulsions such as Marcol 52: Montanide 888 (Marcol is a Trademark of Esso. Montanide is a Trademark of SEPPIC, Paris), squalane or squalene, Adjuvant 65 (containing peanut oil, mannide monooleate and aluminum monostearate), mineral gels such as aluminum hydroxide, aluminum phosphate, calcium phosphate and alum, surfactants such as hexadecylamine, octadecylamine, lysolecithin, dimethyldioctadecylammonium bromide, N,N-dioctadecyl -N',N'-bis(2-hydroxyethyl)propanediamine, methoxyhexadecylglycerol and pluronic polyols, polyanions such as pyran, dextran sulfate, polyacrylic acid and carbopol, peptides and amino acids such as muramyl dipeptide, dimethylglycine, tuftsin and trehalose dimycolate. The variants of the present invention can also be administered following incorporation into liposomes or other micro-carriers, or after conjugation to polysaccharides, proteins or polymers. Other adjuvants suitable for use in the present invention include conjugates comprising the variant together with an integral membrane protein of prokaryotic or eukaryotic origin, such as TraT.

Routes of administration, dosages to be administered as well as frequency of injections are all factors which can be optimized using ordinary skill in-the art. Typically, the initial vaccination is followed some weeks later by one or more "booster" vaccinations, the net effect of which is the production of high titres of antibodies against the variant.

Monoclonal antibodies against the variants of the invention can be prepared using standard techniques for monoclonal antibody production.

The antibody composition is prepared by mixing, preferably homogeneously mixing, antibody with a pharmaceutically acceptable carrier, diluent and/or excipient using standard methods of pharmaceutical preparation.

Conjugates are prepared using standard techniques for conjugate synthesis. The conjugate may be prepared chemically using linking agents as necessary or by recombinant DNA techniques to provide a PAI-2 variant of the invention linked to a cytotoxic drug.

The conjugate composition is prepared by mixing, preferably homogeneously mixing, conjugate with a pharmaceutically acceptable carrier, diluent and/or excipient using standard methods of pharmaceutical preparation.

The amount of conjugate required to produce a single dosage form will vary depending upon the condition to be treated, host to be treated and the particular mode of administration. The specific dose level for any particular patient will depend upon a variety of factors including the activity of the conjugate employed, the age, body weight, general health, sex, and diet of the patient, time of administration, route of administration, rate of excretion, drug combination and the severity of the condition undergoing treatment. The amounts to be used can be determined by standard pharmaceutical techniques.

The conjugate composition may be administered parenterally, in unit dosage formulations containing conventional, non-toxic, pharmaceutically acceptable carriers, diluents, and/or excipients as desired.

Diagnostic kits are prepared by formulating antibodies at appropriate concentration with a pharmaceutically acceptable carrier, diluent, and/or excipient. A positive control standard of a known concentration of a variant of the invention is prepared similarly. The negative standard comprises carrier, diluent, and/or excipient alone. Examples of diagnostic kits include a tumour diagnostic wherein the reagent comprises an antibody of the invention and the positive control comprises a variant of the invention.

PLASMIDS

Various plasmids used in this work were derived from pBTA 438. Plasmid pBTA 438 consists of a 1.6kb cDNA encoding PAI-2 cloned in pUC18 [Yanisch-Perron et al, Gene 33: 103–119 (1985)]. pBTA 438 was used to transform *E. coli* strain JM109 [Yanisch-Perron et al, Gene 33:103–119 (1985)] to yield strain BTA 1445, which was deposited with the American Type Culture Collection of 12301 Parklawn Drive, Rockville, Md. 20852, USA under accession number ATCC 53585 on Feb. 11, 1987.

Plasmid pBTA641 can be derived from pBTA438 as follows. pBTA438 is partially digested with XhoII plus DraI and a 1550bp fragment isolated and ligated to vector pLK58 cut with BglII and SmaI. The resultant plasmid pBTA 446 was linearized with BglII and ligated to a synthetic double stranded 27 mer oligonucleotide having the sequence GATCT(N)$_{16}$ATGGAG (SEQ ID NO: 14), wherein N represents any nucleotide, containing a bacterial ribosome binding site and the initial nucleotides of the native PAI-2 gene, creating plasmid pBTA641. Plasmid pBTA447 is identical to pBTA 641 except that a 26 mer oligonucleotide containing a bacterial ribosome binding site having the sequence GATCT(N)$_{15}$ATGGAG (SEQ ID NO: 13) was used instead of the 27 mer.

Plasmid pMINS71 was derived as follows: the BglII-EcoRl PAI-2 gene fragment from pBTA 641 was inserted into pSp72 (Promega) at the BglII/EcoRl sites; the BglII-SacI PAI-2 gene fragment from this vector was inserted into the HindIII/SacI sites of pGEM4Z (Promega) in a three way ligation with a synthetic adaptor with cohesive HindIII-BglII ends to create pMINS71.

PREPARATIVE EXAMPLE 1

A. Bacterial Expression of PAI-2

Cell extracts of induced (by incubating cells at 42° C.) and uninduced (incubated at 30° C.) *E. coli* K-12 host cells containing pBTA447 and pBTA641 were screened for the presence of PAI-2 using affinity purified monoclonal (Biopool) or polyclonal antibodies to human PAI-2. Biological activity was assessed by a shift in the electrophoretic mobility in the presence of urokinase, characteristic of the formation of a urokinase-PAI-2 complex. A PAI-2 protein band ($M_r$ 46 kD), visualized by western transfer using a monoclonal antibody to human placental inhibitor and iodinated protein A, is present in the induced (42° C.) samples. A lower molecular weight ($M_r$ 37,000) immunologically cross-reactive protein band was also observed indicating possible proteolytic cleavage of the PAI-2 molecule.

B. Purification of 37 kD Form (i) Cell Growth and Lysis

*E. coli* K-12 cells harbouring the plasmid pBTA447 were heat induced at 38° C. in a 10L fermenter for 24 h and the cells then recovered by centrifuging at 17,000 xg for 20 min. A total of 524 g wet weight of cells was recovered from 8L of fermentation broth.

The cells (524 g) were suspended in 1500 ml of 0.1M Na phosphate buffer, pH 7.0 containing 1 mM EDTA and 1 mM PMSF at 4° C. and lysed by four passages through a Martin-Gaulin press at 8000 psi. The press was washed out with 300 ml of the above buffer and the lysate and washes combined. To this solution was added $MgCl_2$ to a final concentration of 2 mM and the solution centrifuged at 17,700 xg for 60 mins. The supernatant (1600 ml) resulting from this centrifugation was recentrifuged at 30,100 xg for 60 mins to remove remaining insoluble material and the supernatant recovered. To this supernatant (1570 ml) was added 574.6 g of solid ammonium sulphate to give a 60% saturated solution, the solution stirred for 15 min. and then centrifuged at 30,000 xg for 30 mins. The resultant pellet, which contains the PAI-2 was divided into eighths and stored at −20° C.

(ii) DEAE-Sephacel Chromatography

One eighth aliquot of 0–60% ammonium sulphate precipitate was dissolved in 200 ml of 0.1M Na phosphate, pH7.0 containing 1 mM EDTA and 0.1 M DTT, and incubated at 37° C. for 90 min. This solution was then diluted to 500 ml with 0.1M Na phosphate, pH 7.0 containing 1 mM EDTA and 0.05% 2-mercaptoethanol and dialysed at 4° C. against the same buffer for 48 h. The dialysed solution was then applied to a DEAE-Sephacel column (4.4 cm×10 cm) equilibrated in the above buffer and eluted until the absorbance at 280 nm returned to base line. A linear 2 liter gradient from 0 to 0.5M NaCl in the same buffer was applied and the column eluted at a flow rate of 2 ml min$^{-1}$ Fractions of 10 ml were collected and 200 µl aliquots analysed by SDS-PAGE and western analysis. The PAI-2 eluted between 58 mM and 81 mM NaCl under these conditions and these fractions were pooled and dialysed against 1 mM Na phosphate, pH 7.0 containing 0.05% 2-mercaptoethanol for 48 h at 4° C.

(iii) Hydroxylapatite Chromatography

The dialysed PAI-2 from the previous step was applied to a 3.2 cm×15 cm column of Biogel HPT equilibrated in 1 mM Na phosphate, pH7.0 containing 0.05% 2-mercaptoethanol and the column washed with the same buffer until the absorbance at 280 nm had returned to baseline. A one liter linear gradient from 1 mM Na phosphate to 200 mM Na phosphate was then applied and the column eluted at a flow rate of 1 ml min$^{-1}$. Six ml fractions were collected. The PAI-2 eluting from the column was detected using SDS-PAGE and western blotting and revealed under reducing conditions two distinct immunologically cross-reactive protein bands. The molecular weights of these two forms of PAI-2 were ca. 46 kD and ca. 37 kD.

(iv) High Pressure Liquid Chromatography

To resolve these two forms of PAI-2 an aliquot from the Biogel HPT column containing PAI-2 was chromatographed on a Vydac C4 HPLC column using a gradient of acetonitrile in 0.1% TFA. This chromatograph revealed two major peaks, the former containing the 37 kD form of PAI-2 and the latter containing the 46 kD form of PAI-2, as determined by non-reducing SDS-PAGE. Amino acid sequencing of the Ca. 37 kD form of PAI-2 revealed the sequence—Lys Gly Ser Tyr Pro Asp Ala Ile Leu Gln Ala Gln Ala Ala Asp (SEQ ID NO: 16).

This sequence corresponds to a form of PAI-2 starting at residue 87 of the mature form of PAI-2 and suggests that the glutamine 86-lysine 87 (Q86-K87) peptide bond is highly susceptible to proteolysis. A similar immunologically cross reactive form of PAI-2 of ca. 37 kD was also observed during the purification of naturally occurring PAI-2 from U937 cells suggesting that proteolytic cleavage at the Q86-K87 peptide bond occurs in both mammalian and bacterial cells and supporting the concept that this bond is highly labile.

C. Purification of 37 kD Form

*E. coli* cells harbouring the plasmid pBTA641 were heat induced at 38° C. in a 10 liter fermenter for 24 hours and the cells then recovered by centrifugation at 17,000 xg for 20 mins.

(i) Cell Lysis

The cell pellet obtained from 5 liters of this fermentation was suspended in 800 ml of 50 mM Na phosphate, containing 1 mM EDTA, 10 mM ε-amino caproic acid (ε-ACA) and 10 mM 2-mercaptoethanol, pH 6.6, and lysed by six passages through a Martin-Gaulin 15 MR homogenizer at 9000 psi. To the resultant lysate (900 ml) was added $MgCl_2$ to 2 mM and the suspension centrifuged at 17,700 xg for 1 hour at 4° C.

(ii) Ammonium Sulphate Precipitation

To the supernatant from the above centrifugation was added solid ammonium sulphate to give a 30% saturated solution. The solution was stirred for 30 mins at 4° C. and then the precipitate removed by centrifugation at 17,700 xg for 1 hour at 4° C. The supernatant (760 ml) was adjusted to 50% saturation by the addition of more solid ammonium sulphate and following stirring at 4° C. for 30 min, the suspension was centrifuged at 17,700 xg for 1 hour at 4° C. The pellet recovered from this precipitation step was dissolved in Buffer B (50 mM Na citrate, 1 mM EDTA, 10 mM ε-ACA and 10 mM 2-mercaptoethanol, pH 5.5) to give a final volume of 200 ml. This solution was then dialysed against 20 volumes of Buffer B overnight at 4° C.

(iii) Phenyl Sepharose Chromatography

The dialysed solution was made 1M in ammonium sulphate and the sample (286 ml) was applied to a Phenyl Sepharose column (5 cm × 19 cm; Vt=373 ml), equilibrated in Buffer A, (Buffer A is Buffer B containing 1M ammonium sulphate) at a flow rate of 100 ml/h. Following loading of the sample the column was washed with Buffer A until the absorbance at 280 nm ($A_{280}$) returned to baseline and then a linear gradient of 800 ml of Buffer A and 800 ml of Buffer B applied. Fractions of 10 ml were collected. Following completion of the gradient the column was washed with 50 mM glycine, pH9.0 until the $A_{280}$ returned to baseline. The PAI-2 eluted in fraction 75–150 as determined by the urokinase inhibition assay of Coleman and Green (in Methods in Enzymology 80: 408–414 1981) and by an immunological dot blot assay. These fractions were pooled (850 ml) and precipitated by the addition of ammonium sulphate to 60% saturation. The pellet was recovered by centrifugation at 17,700 xg for 30 mins at 4° C. and dissolved in Buffer C (25 mM Na borate, 1 mM EDTA, 10 mM ε-ACA, 10 mM 2-mercaptoethanol, pH9.0).

(iv) Sephacryl S200 Chromatography

The solution containing PAI-2 (25 ml) was applied to a Sephacryl S200 column (3.3 cm × 95 cm) equilibrated in Buffer C and eluted at a flow rate of 40 ml/h. Fractions of 6 ml were collected and analysed for PAI-2 by urokinase inhibition, SDS-PAGE and immunological cross-reactivity in a dot blot assay. Fractions containing the PAI-2 (fractions 52–90) were pooled and precipitated with 60% saturated ammonium sulphate. The pellet was recovered by centrifugation at 17,700 xg for 30 mins at 4° C. and redissolved in Buffer A. The pH of this solution was adjusted to 5.5 with HCl and the precipitate which developed was removed by centrifugation at 17,700 xg for 30 mins at 4° C.

(v) Second Phenyl Sepharose Chromatography

The supernatant was applied to a Phenyl Sepharose column (5 cm × 10 cm) at a flow rate of 60 ml/h. Following loading, the column was washed with Buffer A and then a linear gradient of Buffer A and Buffer B applied as described in (iii) above. Following completion of the gradient the column was washed with 50 mM glycine, pH9 and the fractions containing PAI-2 identified by SDS-PAGE and western blotting. Fractions 15–27, containing the PAI-2, were pooled, precipitated with 60% ammonium sulphate and redissolved in 15 ml of Buffer C.

(vi) Second Sephacryl S 200 Chromatography

The sample containing PAI-2 from the second Phenyl Sepharose column above was applied to a Sephacryl S200 column (2.5 cm × 95 cm) equilibrated in Buffer C and eluted at a flow rate of 30 ml/h. Fractions of 2.6 ml were collected and analysed for PAI-2 by SDS-PAGE.

(viii) Reverse Phase HPLC

The SDS-PAGE of the fractions from the second Sephacryl S200 column showed the presence of two proteins with approximate molecular weights of ca 46 kD and 37 kD when electrophoresed in the presence of 2-mercaptoethanol. These protein bands are similar to those observed in "B. Purification of 37 kD Form". To resolve these two forms, a 90 μl aliquot of fraction 106 from the second Sephacryl S-200 column above was chromatographed on a Vydac $C_4$ reverse phase HPLC column using a gradient of acetonitrile in 0.1% TFA. The leading edge of the major absorbance peak eluted from this column contained primarily the 37 kD protein. Amino acid sequencing of this fraction revealed an N-Terminal sequence of F M Q Q I Q K G S Y (Phe Met Gln Gln Ile Gln Lys Gly Ser Tyr: SEQ ID NO: 17) which corresponds to the sequence of PAI-2 starting at amino acid residue 81. It was therefore concluded that this form of PAI-2 arose from proteolytic cleavage of the mature form of PAI-2 at the glycine 80-phenylalanine 81 bond.

The observation that purification of PAI-2 overexpressed in *E. coli* by this alternative method and, in particular, the inclusion of ε-ACA as an inhibitor of lysine specific proteases, protected PAI-2 from cleavage at the Q86-K87 bond but not cleavage at a region only six amino acids upstream of this site, reinforces the view that this region of the molecule is highly susceptible to protease cleavage.

D. Purification of 37 kD Form

To determine whether the proteolysis observed above could be prevented by expression in an alternative host PAI-2 was overexpressed in the baculovirus insect cell system (Lucknow and Summers, Biotechnology 6: 47–55, 1988). The expressed product was purified essentially as described in "C. Purification of 37 kD Form" using steps (i) through (iv) except that the 50% ammonium sulphate precipitation step in (ii) was omitted. The PAI-2 eluting from the Sephacryl S-200 column was detected by SDS-PAGE and western blotting under reducing conditions. This analysis showed the presence of both a 46 kD and a 37 kD form of PAI-2, indicating that proteolytic cleavage of the molecule was occurring as observed previously. To further define the site of this cleavage the PAI-2 pool obtained from the Sephacryl S-200 chromatography step was dialysed against 20 mM glycine, 10 mM EDTA and 10 mM 2-mercaptoethanol, pH9.0 and the sample (30 ml) then applied to a Q-Sepharose column (0.9 cm×24 cm) at a flow rate of 60 ml/h. The PAI-2 eluted unretarded from this column and on SDS-PAGE revealed two Coomassie blue staining bands of Mr=ca 37 kD and ca 46 kD. N-terminal amino acid sequencing of an aliquot of this material revealed a single sequence as shown below G F M Q Q I Q K G S Y P D A I (i.e. Gly Phe Met Gln Gln Ile Gln Lys Gly Ser Tyr Pro Asp Ala Ile: SEQ ID NO: 18). No authentic N-terminal sequence for the full length PAI-2 was observed, indicating that the 46 kD form of PAI-2 when expressed in insect cells contains a blocked N-terminus. Similar results have been observed with full length PAI-2 isolated from U937 cells (Kruithof et al J. Biol Chem 216: 11207–11213 1986) and from placenta (Andreasen et al 261: 7644–7651 1986). The observed sequence is consistent with proteolytic cleavage occurring between cysteine 79 and glycine 80, only one peptide bond upstream from the G80-F81 cleavage site observed with PAI-2 purified from *E. coli* in "C. Purification of 37 kD Form".

These results further confirm the high degree of proteolytic susceptibility of this region of the PAI-2 molecule. E. Purification of the K87A variant of PAI-2

Creation of a variant PAI-2, wherein amino acid residue 87 was changed from Lys to Ala, was achieved by site-directed mutagenesis, after transferring the PAI-2 coding region to the phage M13 vector mp18. Preparation and use of single-stranded phage DNA, as well as the use of the two oligonucleotides containing the mutated sequence [(5'-CAG CAG ATC CAG GCA GGT AGT TAT CCT-3' (SEQ ID NO: 19), 5'-AGG ATA ACT ACC TGC CTG GAT CTG CTG-3' (SEQ ID NO: 21) complement of SEQ ID NO: 19; with the amino acid translation shown in (SEQ ID NO: 20) ], were carried out as previously described (Amersham; oligonucleotide-directed in vitro mutagenesis system).

The K87A variant of PAI-2 was purified from a 1 liter culture of *E. coli* K-12 cells harbouring the plasmid pBTA674. This plasmid is identical to pBTA641 but with the PAI-2 DNA replaced with the variant form of PAI-2.

The purification was performed essentially as described in "C. Purification of 37 kD Form", steps (i) through (iv) except that the 50% ammonium sulphate precipitation in step (ii) was omitted. Analysis of the fractions eluted from the Sephacryl S-200 column by reducing SDS-PAGE and western blotting indicated the presence of both a 46 kD and a 37 kD form of PAI-2, indicating that mutagenesis of lysine 87 to an alanine residue failed to prevent cleavage of the PAI-2 molecule in the region previously identified as protease sensitive (see B. Purification of 37 kD form).

EXAMPLE 1

Deletion of Protease Sensitive Site

Figure 2A:
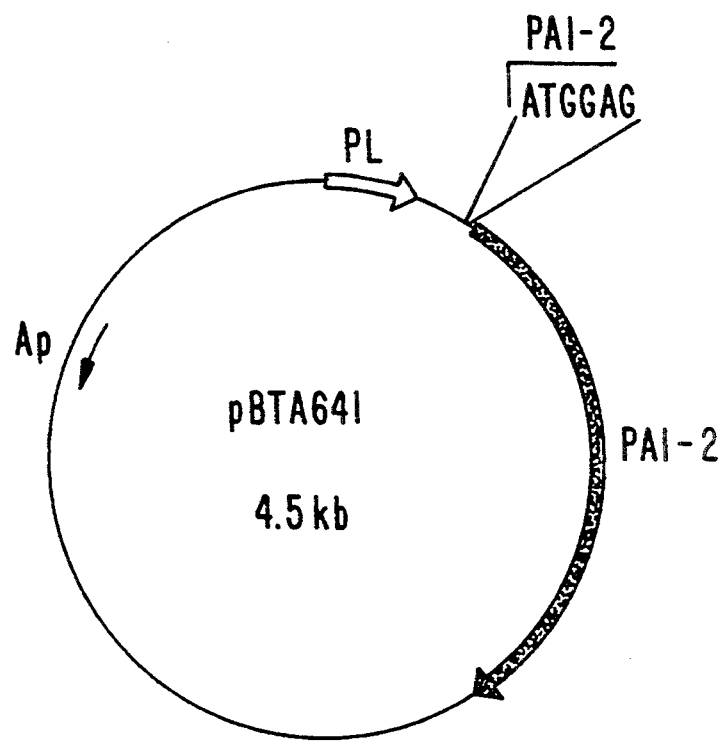
FIG. 2 Bacterial (pBTA641) and baculovirus transfer vector (pAc373) used in expression of PAI-2 and its variants in *E. coli* K-12 and insect cells respectively.
Figure 2B:
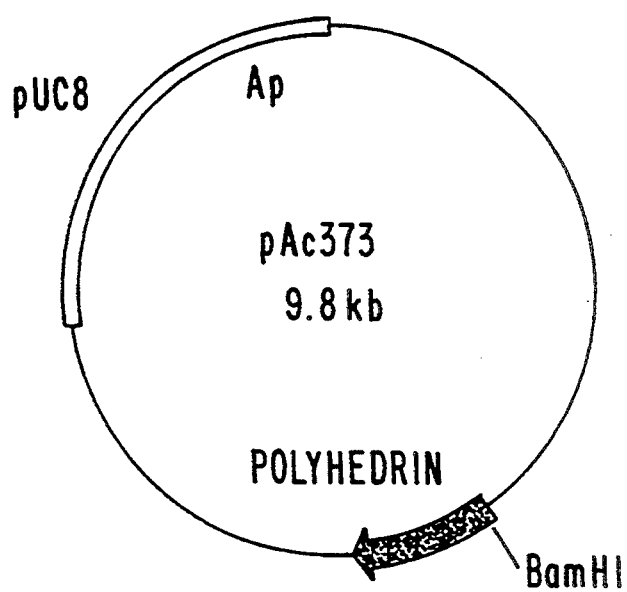
Figure 6:
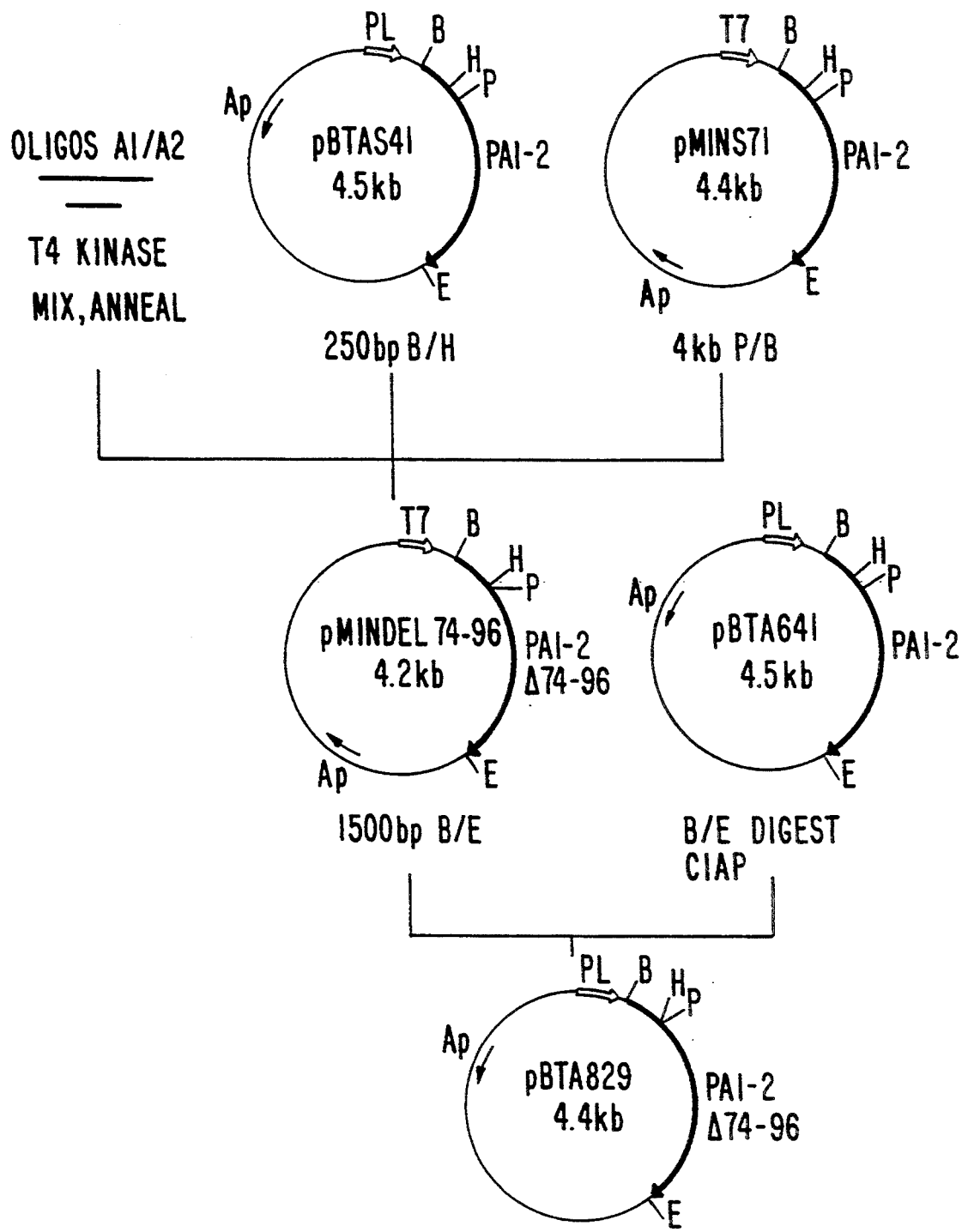
FIG. 6 Construction of plasmid pBTA829 containing the deletion variant, Δ74–96. (Abbreviations used: B, BglII; H, HinfI; P, PstI; E, EcoRI; $P_L$, leftwards promoter of bacteriophage lambda; $T_7$, promoter from bacteriophage $T_7$; Ap, ampicillin resistance gene; CIAP, calf intestine alkaline phosphatase)

The HinfI-PstI segment spanning the protease sensitive site in PAI-2 was replaced by synthetic oligonucleotides with cohesive HinfI and PstI ends (see FIG. 5), creating a variant PAI-2 in which amino acids 74 to 96 inclusive were deleted. The events involved in the construction of this deletion variant are illustrated in FIG. 6. In essence, the deletion variant was assembled in an intermediate vector by a three way ligation between a BglII-HinfI fragment from pBTA641, a PstI-BglII fragment from pMINS71 and the annealed oligonucleotides A1 (SEQ ID NO: 7) and A2 (SEQ ID NO: 8). The assembled deletion PAI-2 was then excised from the intermediate vector and exchanged with native PAI-2 in pBTA641 to create pBTA 829.

Oligonucleotides (FIG. 5 SEQ ID NOS: 7 and 8) were synthesized on an Applied Biosystems DNA synthesizer (Model 380A), and purified through a polyacrylamide gel. Complementary oligonucleotides (A1: SEQ ID NO: 7 and A2 SEQ ID NO: 8) were mixed in a 1:1 molar ratio and phosphorylated using 5 units T4 polynucleotide kinase in 65 mM Tris-Cl pH 7.5, 10 mM MgCl$_2$, 5 mM dithiothreitol, 1 mM ATP. The mixture was heated to 65° C. for 10 minutes and cooled slowly to room temperature to allow annealing to take place. The various restriction fragments were prepared as follows. Restriction enzyme digests of purified plasmid DNA were carried out in buffers recommended by the supplier. Required DNA fragments were separated from the plasmid by gel electrophoresis through 0.8–1.5% Sea-Plaque agarose (FMC Corporation) in Tris-acetate buffer (Maniatis et al, 1982). Fragments were visualized by staining with ethidium bromide and UV transillumination. The band of agarose containing the appropriate fragment was sliced out of the gel, melted at 65° C. and the DNA was extracted three times with phenol/chloroform/isoamyl alcohol. The DNA was then precipitated with ethanol.

Vectors were typically prepared as follows. Plasmid DNA was digested with the appropriate restriction enzymes, the digest was extracted with an equal volume of phenol/chloroform/isoamyl alcohol and the DNA precipitated with 2.5 volumes of ethanol. The digested DNA was resuspended in 50 mM Tris-Cl pH 9.0, 1 mM MgCl$_2$, 0.1 mM ZnCl$_2$, 1 mM spermidine and incubated with 1–2 units calf intestinal alkaline phosphatase (Boehringer Mannheim) for 30–60 mins at 37° C. The enzyme was heat killed at 70° C. for 15 minutes then the DNA was extracted with phenol/chloroform/isoamyl alcohol and precipitated with ethanol.

Ligations were carried out as follows. Vector and insert DNAs were mixed at a molar ratio of between 1:1 and 1:5 (1:10 if the insert was smaller then 100 bp) in 1 mM ATP, 10 mM MgCl$_2$, 5 mM DTT, 65 mM Tris-Cl-pH7.5 in a volume of 20 [l. Ligations were carried out at 16° C. overnight with 0.5–1 unit T4 DNA ligase (Boehringer Mannheim). From ligation mixes 5–10 μl was removed for transformation into a competent *E. coli* K12 host (Hanahan, J. Mol Biol 166: 557–580, 1983). Transformants were selected by plating onto tryptone-soya agar plates containing 100 μg/ml ampicillin.

Plasmid DNA was extracted from individual colonies and the correct recombinant plasmids identified by restriction analysis. The region of the PAI-2 gene where the deletion was made was sequenced to confirm the changes. Sequencing was carried out on double-stranded plasmid DNA using the Sequenase DNA Sequencing Kit (USB) as described in the instruction manual. The primer used was the T7 primer (Promega).

Bacterial Constructions and Expression

The complete coding sequence of PAI-2 and the deletion variant were placed under the control of the lambda $P_L$ promoter in the vector pLK58, with a synthetic oligonucleotide upstream of the ATG providing a bacterial ribosome binding site at an appropriate distance from the start codon, giving plasmids pBTA 641 encoding the native PAI-2 sequence and pBTA829 encoding the deletion variant Δ74–96.

These plasmids were used to transform an E. coli K-12 ΔHI Δtrp host which contained the thermolabile repressor of lambda, cI857. Transformed cells were grown overnight in TSB medium (Oxoid) at 28° C. Cells were then diluted in MEB medium (Mott et al Proc. Natl. Acad. Sci. 82: 88–92 1985), grown at 28° C. to an $OD_{600}$ of 1.0 when prewarmed (48° C.) MEB medium was added in equal volume to equilibrate the temperature to 38° C. Following 4 hours of growth at 38° C. the cells were harvested by centrifugation at 8000×g for 15 mins. Cell pellets were resuspended in Behs buffer (10 mM p-chloromercuro benzoic acid, 10 mM EDTA (Na)$_2$, 10 mM 1,10-phenathioline, 100 mM phosphate, pH7.0) and lysed by two passes through a french press at 16,000 psi (on ice). The supernatant from lysed cells was clarified by centrifugation at 8000 xg for 15 mins and tested for the presence of PAI-2 using affinity purified monoclonal (Biopool) or polyclonal antibodies to human PAI-2. Biological activity was also assessed by a shift in the electrophoretic mobility in the presence of urokinase, characteristic of the formation of a urokinase—PAI-2 complex, as described below.

U-PA Binding Experiment

The ability of the deletion variant of PAI-2 described above to bind to urokinase was determined in a urokinase binding experiment. Since the Δ74–96 variant is a significantly altered molecule compared to the native PAI-2 it is not possible to predict whether the variant has biological activity or not. Urokinase (LMW, American Diagnostica) was added to clarified supernatant from lysed cells expressing native (i.e. expressed from pBTA641) or variant Δ74–96 (i.e. expressed from pBTA829) PAI-2, or no PAI-2 (i.e. cells containing pBTA 836). As a negative control, lysates were used without the addition of urokinase. Plasmid pBTA 836 was derived from pBTA 641 by digestion with BglII and EcoRl to excise the PAI-2 gene, followed by a fill-in reaction using Klenow enzyme and a ligation reaction to reform an intact plasmid lacking the PAI-2 gene.

Binding was allowed to proceed at room temperature for 90 minutes. Samples were then boiled for 3 minutes after the addition of a buffer containing SDS and 2-mercaptoethanol and analysed by SDS-PAGE and western blotting, using either a goat polyclonal antibody against PAI-2 (FIG. 7A), or rabbit polyclonal antibody against urokinase (FIG. 7B). Bound antibody was detected using a second antibody-HRP conjugate directed against the primary antibody.

FIG. 7 shows the results of such an experiment. The addition of urokinase to lysates containing native or variant Δ74–96 PAI-2 resulted in the formation of an SDS stable complex of approximately 69 kD that reacted with either polyclonal antibody directed against PAI-2 (FIG. 7A, lanes c and e) or antibody directed against urokinase (FIG. 7B, lanes c and e). In the absence of urokinase, or in cell lysates lacking PAI-2, such a complex could not be detected using either antibody against PAI-2 (FIG. 7A, lanes b, d, f, g) or antibody against urokinase (FIG. 7B, lanes b, d, f, g). These results are characteristic of the formation of a urokinase-PAI-2 complex and indicate that both the native PAI-2 and the variant Δ74–96 PAI-2 are capable of binding urokinase and hence possess biochemical activity.

Elimination of Proteolytic Sensitivity

In E. coli cells expressing native PAI-2 (i.e. from pBTA 641) the major products detected by PAI-2 specific antibody following SDS-PAGE and western transfer are a 46 kD form, representing native PAI-2, and a 37 kD form representing a degradation product (FIG. 7A, lane b). In cells expressing the variant Δ74–96 PAI-2 (i.e. from pBTA 829) the 37 kD degradation product cannot be detected (FIG. 7A, lane d). These results show that the variant Δ74–96 PAI-2 does not possess the proteolytic sensitivity of the native PAI-2.

EXAMPLE 2

Deletion of Protease Sensitive Site

DNA sequences encoding amino acids 66–98 inclusive were deleted from the PAI-2 coding region using the polymerase chain reaction (PCR) technique of site-directed mutagenesis by overlap extension (Ho et al. Gene 77: 51–59, 1989). The oligonucleotides used in the PCR reactions are shown in FIG. 8 (SEQ ID NOS: 9, 10 and 11) and an outline of the construction of this deletion variant illustrated in FIG. 9.

In brief, the PAI-2 DNA was transferred to an intermediate vector which was used in PCR reactions to generate a Bgl II/PstI fragment in which the sequences encoding amino acids 66–98 inclusive had been deleted. The PCR generated Bgl II/Pst I deletion fragment was exchanged for the native Bgl II/Pst I fragment in the intermediate vector and the entire Bgl II/Pst I region from five independent transformants sequenced. From one of these transformants, in which the only differences from the native PAI-2 was the deletion of sequences encoding amino acids 66–98 inclusive, the PAI-2 DNA was recovered and ligated into the vector pLK 58 to create pBTA 840.

Oligonucleotides (FIG. 8: SEQ ID NOS: 9, 10 and 11) were synthesized on an Applied Biosystems DNA synthesizer (Model 380A), with the trityl group left on, and purified on oligonucleotide purification cartridges (Applied Biosystems, Cat. No. 400771) according to the manufacturer's instructions. One oligo, Sp6 primer, was purchased from Promega.

PCR reactions were in 50 mM KCl, 10 mM tris-HCl pH 8.3, 1.5 mM Mg Cl$_2$, 0.01% gelatin w/v, 200 μM dNTPs, 2.5U amplitaq (Perkin-Elmer Cetus), using 100 pmoles of oligonucleotides and 0.35 pmoles of Eco R1 linearized PAI-2 plasmid. Reactions were carried out on a Gene Machine (Innovonics) set for 25 cycles with 1 minute denaturation (94° C.), 1 minute annealing (50° C.) and 1 minute extension (74° C.). PCR products were separated from oligonucleotides either on Sephacryl S-200 columns or by gel electrophoresis through 1.5% sea-plaque agarose (FMC Corporation) in tris-acetate buffer (Maniatis et al 1982), followed by staining with ethidium bromide, visualization on a UV transilluminator and purification from the agarose gel slice on NACS columns (BRL) according to the manufacturer's instructions.

Other required DNA fragments were separated from plasmid DNA by gel electrophoresis through 0.8–1.5%, sea-plaque agarose and purified as described above for PCR products.

Vectors were typically prepared as follows. Plasmid DNA was digested with the appropriate restriction enzymes for 1 to 2 hrs. at 37° C. Calf intestinal alkaline phosphatase (CIAP Boehringer Mannhelm, 1 to 2 units) was added directly to the restriction digest and the incubation continued at 37° C. for 1 hour. In some cases, when restriction enzymes that yielded flush or 3' overhang ends were used, the incubation with CIAP was for 30 minutes at 37° C. and 30 minutes at 50° C. The CIAP enzyme was heat killed at 70° C. for 15 minutes and the DNA was extracted with phenol/chloroform/isoamyl alcohol and precipitated with ethanol.

Ligations and transformation of E. coli K12 hosts were as described in Example 1. In some cases ligations were at 4° C. for 48 hours or 16° C. for 4 to 6 hours.

Sequencing of the Bgl II/Pst I regions were performed on double-stranded plasmid DNA, after alkali denaturation, using a Multiwell Microtitre Sequencing System Kit (Amersham) as described in the instruction manual. The primer used was the Sp6 primer (Promega).

Plasmids used in this-work were derived as described above.

Expression in E. coli

Plasmid pBTA 840 was used to transform an E. coli $\Delta H_1 \Delta trp$ host which contained the thermolabile repressor of lambda, cI857. A single transformant was grown overnight in TSB medium at 28° C. and the resulting culture used to innoculate a 10 liter fermenter. The E. coli cells were heat induced at 38° C. for 24 hrs. and the cells recovered by centrifugation at 17,000 g for 20 min.

Purification of Δ66–98 and Δ74–96 PAI-2

The PAI-2 variants Δ66–98 and Δ74–96 can be purified from cells of E. coli expressing the molecule using a combination of the procedures used in the purification of the native molecule viz processes involving phenyl-sepharose chromatography, Sephacryl S200 chromatography, ion exchange chromatography and/or reverse phase HPLC. These procedures are described in International Patent Application No PCT/AU85/00191 (WO 86/01212) and International Patent Application No PCT/AU87/00068 (WO 87/05628) and the results of purifying Δ66–98 are illustrated in FIG. 10.

U-PA, two chain t-PA, and single chain t-PA binding experiment

The ability of the purified deletion variant Δ66–98 to bind to U-PA, to two chain t-PA and to single chain t-PA was examined in a binding experiment similar to that described in Example 1. The binding characteristics of Δ66–98 PAI-2 (SEQ ID NO: 3) were compared to those exhibited by native PAI-2 (i.e. as expressed from pBTA641) (SEQ ID NO: 1), the Δ74–96 variant (i.e. as expressed from pBTA829) (SEQ ID NO: 2) and to the second form of native PAI-2 that differs by three amino acids from the PAI-2 expressed from pBTA641 (Schleuning et. al. Mol. Cell. Biol. 2: 4564–4567, 1987). The alternative native PAI-2 was expressed from pBTA 683. Plasmid pBTA 683 was derived from pBTA641 by site directed mutagenesis that changed 3 amino acids to that found in the second form of PAI-2. [Schleuning et al. Mol. Cell Biol. 7: 4564–4567 (1987)].

The various PAI-2s (0.25 μg each) were incubated with either u-PA (3.75 μg, Behring), two chain t-PA or single chain t-PA (3.75 μg each, American Diagnostica) at room temperature for 160 minutes in 25 mM Tris-HCl pH7.5, 75 mM NaCl, 2.5 mM EDTA and 0.5% TX-100. Samples were analysed on 10% SDS-polyacrylamide gels followed by western blotting. Blots were probed with a goat polyclonal antibody against PAI-2 and bound antibody detected by an anti-goat-HRP conjugate (FIG. 11).

All PAI-2s, (the two native forms and the two deletion variants) displayed identical binding characteristics. Thus, on incubation with either U-PA, two chain t-PA or single chain t-PA high molecular weight SDS stable forms of PAI-2 were seen. Such high molecular weight forms are characteristic of the formation of complexes between PAI-2 and these plasminogen activators.

Elimination of Proteolytic Sensitivity

As with the variant Δ74–96, the 37 kD degradation product observed on purification of native PAI-2, was not found in purified preparations of the variant Δ66–98 (FIG. 10).

INDUSTRIAL APPLICABILITY

The PAI-2 variants of the invention can be used as therapeutic and diagnostic agents in patients with tumours, or suffering from chronic inflammatory conditions such as rheumatoid arthritis.

Other conditions where the application of a specific PA inhibitor may be of use include diseases or conditions such as osteoarthritis, multiple sclerosis, colitis ulcerosa, SLE-like disease, psoriasis, pemphigus, corneal ulcer, gastroduodenal ulcer, purpura, periodontitis, haemorrhage and muscular dystrophy. A specific PA inhibitor would also be useful as an adjunct to thrombolytic therapy involving PAs in order to reduce the incidence and severity of the side effect of such treatment viz. systemic fibrinolysis. Finally, a PA inhibitor could have a significant role in skin wound healing and tissue repair especially since two trypsin inhibitors have been shown to enhance formation of connective tissue with increased tensile strength of the wound tissue [Kwaan, HC and Astrup, T (1969) Exp. Molec. Path 11, 82] and keratinocytes are known to produce both uPA and tPA [Grondahl-Hansen, J et al. (1988) J. Invest Dermatol.].

Antibodies against variants of the invention should be useful in the detection or monitoring of disease states or conditions such as monocytic leukaemia, cancer, foetal development and chronic inflammatory diseases.

We claim:

1. A plasminogen activator inhibitor type 2 variant in which the 66–98 amino acid residue region of SEQ ID NO: 2 has been altered to eliminate at least one protease sensitive site, which variant maintains biological activity of plasminogen activator inhibitor type 2 of SEQ ID NO: 2 amino acids up to 65 and from 99 of plasminogen activator inhibitor type 2 in frame.

2. A plasminogen activator inhibitor type 2 variant according to claim 1, which variant is a deletion variant in which at least one amino acid residue in the 66–98 region of SEQ ID NO: 2 has been deleted.

3. The plasminogen activator inhibitor type 2 variant according to claim 1, wherein said variant is variant Δ74–96 of SEQ ID NO: 4 in which amino acids 74–96 inclusive of plasminogen activator inhibitor type 2 have been deleted.

4. The plasminogen activator inhibitor type 2 variant according to claim 1, wherein said variant is variant Δ66–98 of SEQ ID NO: 6 in which amino acids 66–98 inclusive of plasminogen activator inhibitor type 2 have been deleted.

5. A plasminogen activator inhibitor type 2 variant according to claim 1, wherein said variant is labelled with one of a radioisotope and a chemical agent.

6. A diagnostic composition comprising at least one plasminogen activator inhibitor type 2 variant according to claim 1 together with a pharmaceutically acceptable carrier, excipient, or diluent.

7. A diagnostic composition comprising at least one plasminogen activator inhibitor type 2 variant according to claim 5 together with a pharmaceutically acceptable carrier, excipient, or diluent.

8. An antibody specific to a plasminogen activator inhibitor type 2 variant according to claim 1.

9. A polyclonal antibody according to claim 8.

10. A monoclonal antibody according to claim 8.

11. A process for preparing an antibody specific to a plasminogen. activator inhibitor type 2 variant according to claim 1, which process comprises immunizing an immuno-competent host with an effective amount of a a plasminogen activator inhibitor type 2 variant according to claim 1.

12. An antibody composition comprising an antibody according to claim 8 together with a pharmaceutically acceptable carrier, diluent, or excipient.

13. A diagnostic reagent comprising an antibody according to claim 8 or an antibody according to claim 8 together with a pharmaceutically acceptable carrier, diluent, or excipient.

14. A diagnostic kit comprising any of the following: a variant according to claim 1 as a standard, or an antibody specific to a plasminogen activator inhibitor type 2 variant according to claim 1.

---

SEQUENCE LISTING ( 1 ) GENERAL INFORMATION:

( i i i ) NUMBER OF SEQUENCES: 21

( 2 ) INFORMATION FOR SEQ ID NO:1:

( i ) SEQUENCE CHARACTERISTICS:
( A ) LENGTH: 1610 base pairs
( B ) TYPE: nucleic acid
( C ) STRANDEDNESS: double
( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
( A ) ORGANISM: Homo sapiens
( G ) CELL TYPE: Monocyte
( H ) CELL LINE: U937

( v i i ) IMMEDIATE SOURCE:
( B ) CLONE: BTA 1445

( v i i i ) POSITION IN GENOME:
( A ) CHROMOSOME/SEGMENT: 18
( B ) MAP POSITION: 18q21-q23

( i x ) FEATURE:
( A ) NAME/KEY: CDS
( B ) LOCATION: 49..1296
( D ) OTHER INFORMATION: /product="human plasminogen activator inhibitor type 2 protein"

( x i ) SEQUENCE DESCRIPTION: SEQ ID NO:1:

```
GTCAGACAGC AACTCAGAGA ATAACCAGAG AACAACCAGA TTGAAACA ATG GAG GAT    57
                                                     Met Glu Asp
                                                       1

CTT TGT GTG GCA AAC ACA CTC TTT GCC CTC AAT TTA TTC AAG CAT CTG    105
Leu Cys Val Ala Asn Thr Leu Phe Ala Leu Asn Leu Phe Lys His Leu
      5                  10                  15

GCA AAA GCA AGC CCC ACC CAG AAC CTC TTC CTC TCC CCA TGG AGC ATC    153
Ala Lys Ala Ser Pro Thr Gln Asn Leu Phe Leu Ser Pro Trp Ser Ile
 20                  25                  30                  35

TCG TCC ACC ATG GCC ATG GTC TAC ATG GGC TCC AGG GGC AGC ACC GAA    201
Ser Ser Thr Met Ala Met Val Tyr Met Gly Ser Arg Gly Ser Thr Glu
                 40                  45                  50

GAC CAG ATG GCC AAG GTG CTT CAG TTT AAT GAA GTG GGA GCC AAT GCA    249
Asp Gln Met Ala Lys Val Leu Gln Phe Asn Glu Val Gly Ala Asn Ala
             55                  60                  65
```

| | | | | | | | | | | | | | | | | |
|---|---|---|---|---|---|---|---|---|---|---|---|---|---|---|---|---|
| GTT | ACC | CCC | ATG | ACT | CCA | GAG | AAC | TTT | ACC | AGC | TGT | GGG | TTC | ATG | CAG | 297 |
| Val | Thr | Pro | Met | Thr | Pro | Glu | Asn | Phe | Thr | Ser | Cys | Gly | Phe | Met | Gln | |
| | | 70 | | | | 75 | | | | | 80 | | | | | |
| CAG | ATC | CAG | AAG | GGT | AGT | TAT | CCT | GAT | GCG | ATT | TTG | CAG | GCA | CAA | GCT | 345 |
| Gln | Ile | Gln | Lys | Gly | Ser | Tyr | Pro | Asp | Ala | Ile | Leu | Gln | Ala | Gln | Ala | |
| | 85 | | | | | 90 | | | | | 95 | | | | | |
| GCA | GAT | AAA | ATC | CAT | TCA | TCC | TTC | CGC | TCT | CTC | AGC | TCT | GCA | ATC | AAT | 393 |
| Ala | Asp | Lys | Ile | His | Ser | Ser | Phe | Arg | Ser | Leu | Ser | Ser | Ala | Ile | Asn | |
| 100 | | | | | 105 | | | | | 110 | | | | | 115 | |
| GCA | TCC | ACA | GGG | AAT | TAT | TTA | CTG | GAA | AGT | GTC | AAT | AAG | CTG | TTT | GGT | 441 |
| Ala | Ser | Thr | Gly | Asn | Tyr | Leu | Leu | Glu | Ser | Val | Asn | Lys | Leu | Phe | Gly | |
| | | | | 120 | | | | | 125 | | | | | 130 | | |
| GAG | AAG | TCT | GCG | AGC | TTC | CGG | GAA | GAA | TAT | ATT | CGA | CTC | TGT | CAG | AAA | 489 |
| Glu | Lys | Ser | Ala | Ser | Phe | Arg | Glu | Glu | Tyr | Ile | Arg | Leu | Cys | Gln | Lys | |
| | | | 135 | | | | | 140 | | | | | 145 | | | |
| TAT | TAC | TCC | TCA | GAA | CCC | CAG | GCA | GTA | GAC | TTC | CTA | GAA | TGT | GCA | GAA | 537 |
| Tyr | Tyr | Ser | Ser | Glu | Pro | Gln | Ala | Val | Asp | Phe | Leu | Glu | Cys | Ala | Glu | |
| | | | 150 | | | | | 155 | | | | | 160 | | | |
| GAA | GCT | AGA | AAA | AAG | ATT | AAT | TCC | TGG | GTC | AAG | ACT | CAA | ACC | AAA | GGC | 585 |
| Glu | Ala | Arg | Lys | Lys | Ile | Asn | Ser | Trp | Val | Lys | Thr | Gln | Thr | Lys | Gly | |
| | 165 | | | | | 170 | | | | | 175 | | | | | |
| AAA | ATC | CCA | AAC | TTG | TTA | CCT | GAA | GGT | TCT | GTA | GAT | GGG | GAT | ACC | AGG | 633 |
| Lys | Ile | Pro | Asn | Leu | Leu | Pro | Glu | Gly | Ser | Val | Asp | Gly | Asp | Thr | Arg | |
| 180 | | | | | 185 | | | | | 190 | | | | | 195 | |
| ATG | GTC | CTG | GTG | AAT | GCT | GTC | TAC | TTC | AAA | GGA | AAG | TGG | AAA | ACT | CCA | 681 |
| Met | Val | Leu | Val | Asn | Ala | Val | Tyr | Phe | Lys | Gly | Lys | Trp | Lys | Thr | Pro | |
| | | | | 200 | | | | | 205 | | | | | 210 | | |
| TTT | GAG | AAG | AAA | CTA | AAT | GGC | CTT | TAT | CCT | TTC | CGT | GTA | AAC | TCG | GCT | 729 |
| Phe | Glu | Lys | Lys | Leu | Asn | Gly | Leu | Tyr | Pro | Phe | Arg | Val | Asn | Ser | Ala | |
| | | | 215 | | | | | 220 | | | | | 225 | | | |
| CAG | CGC | ACA | CCT | GTA | CAG | ATG | ATG | TAC | TTG | CGT | GAA | AAG | CTA | AAC | ATT | 777 |
| Gln | Arg | Thr | Pro | Val | Gln | Met | Met | Tyr | Leu | Arg | Glu | Lys | Leu | Asn | Ile | |
| | | 230 | | | | | 235 | | | | | 240 | | | | |
| GGA | TAC | ATA | GAA | GAC | CTA | AAG | GCT | CAG | ATT | CTA | GAA | CTC | CCA | TAT | GCT | 825 |
| Gly | Tyr | Ile | Glu | Asp | Leu | Lys | Ala | Gln | Ile | Leu | Glu | Leu | Pro | Tyr | Ala | |
| | | 245 | | | | | 250 | | | | | 255 | | | | |
| GGA | GAT | GTT | AGC | ATG | TTC | TTG | TTG | CTT | CCA | GAT | GAA | ATT | GCC | GAT | GTG | 873 |
| Gly | Asp | Val | Ser | Met | Phe | Leu | Leu | Leu | Pro | Asp | Glu | Ile | Ala | Asp | Val | |
| 260 | | | | | 265 | | | | | 270 | | | | | 275 | |
| TCC | ACT | GGC | TTG | GAG | CTG | CTG | GAA | AGT | GAA | ATA | ACC | TAT | GAC | AAA | CTC | 921 |
| Ser | Thr | Gly | Leu | Glu | Leu | Leu | Glu | Ser | Glu | Ile | Thr | Tyr | Asp | Lys | Leu | |
| | | | | 280 | | | | | 285 | | | | | 290 | | |
| AAC | AAG | TGG | ACC | AGC | AAA | GAC | AAA | ATG | GCT | GAA | GAT | GAA | GTT | GAG | GTA | 969 |
| Asn | Lys | Trp | Thr | Ser | Lys | Asp | Lys | Met | Ala | Glu | Asp | Glu | Val | Glu | Val | |
| | | | 295 | | | | | 300 | | | | | 305 | | | |
| TAC | ATA | CCC | CAG | TTC | AAA | TTA | GAA | GAG | CAT | TAT | GAA | CTC | AGA | TCC | ATT | 1017 |
| Tyr | Ile | Pro | Gln | Phe | Lys | Leu | Glu | Glu | His | Tyr | Glu | Leu | Arg | Ser | Ile | |
| | | 310 | | | | | 315 | | | | | 320 | | | | |
| CTG | AGA | AGC | ATG | GGC | ATG | GAG | GAC | GCC | TTC | AAC | AAG | GGA | CGG | GCC | AAT | 1065 |
| Leu | Arg | Ser | Met | Gly | Met | Glu | Asp | Ala | Phe | Asn | Lys | Gly | Arg | Ala | Asn | |
| | 325 | | | | | 330 | | | | | 335 | | | | | |
| TTC | TCA | GGG | ATG | TCG | GAG | AGG | AAT | GAC | CTG | TTT | CTT | TCT | GAA | GTG | TTC | 1113 |
| Phe | Ser | Gly | Met | Ser | Glu | Arg | Asn | Asp | Leu | Phe | Leu | Ser | Glu | Val | Phe | |
| 340 | | | | | 345 | | | | | 350 | | | | | 355 | |
| CAC | CAA | GCC | ATG | GTG | GAT | GTG | AAT | GAG | GAG | GGC | ACT | GAA | GCA | GCC | GCT | 1161 |
| His | Gln | Ala | Met | Val | Asp | Val | Asn | Glu | Glu | Gly | Thr | Glu | Ala | Ala | Ala | |
| | | | | 360 | | | | | 365 | | | | | 370 | | |
| GGC | ACA | GGA | GGT | GTT | ATG | ACA | GGG | AGA | ACT | GGA | CAT | GGA | GGC | CCA | CAG | 1209 |
| Gly | Thr | Gly | Gly | Val | Met | Thr | Gly | Arg | Thr | Gly | His | Gly | Gly | Pro | Gln | |
| | | | | 375 | | | | | 380 | | | | | 385 | | |
| TTT | GTG | GCA | GAT | CAT | CCT | TTT | CTT | TTT | CTT | ATT | ATG | CAT | AAG | ATA | ACC | 1257 |

|     |     |     |     |     |     |     |     |     |     |     |     |     |     |     |     |
|-----|-----|-----|-----|-----|-----|-----|-----|-----|-----|-----|-----|-----|-----|-----|-----|
| Phe | Val | Ala | Asp | His | Pro | Phe | Leu | Phe | Leu | Ile | Met | His | Lys | Ile | Thr |
|     |     | 390 |     |     |     | 395 |     |     |     |     | 400 |     |     |     |     |

```
AAC TGC ATT TTA TTT TTC GGC AGA TTT TCC TCA CCC TAAAACTAAG                1303
Asn Cys Ile Leu Phe Phe Gly Arg Phe Ser Ser Pro
    405                     410                 415

CGTGCTGCTT CTGCAAAAGA TTTTTGTAGA TGAGCTGTGT GCCTCAGAAT TGCTATTTCA         1363

AATTGCCAAA AATTTAGAGA TGTTTTCTAC ATATTTCTGC TCTTCTGAAC AACTTCTGCT         1423

ACCCACTAAA TAAAACACA GAAATAATTA GACAATTGTC TATTATAACA TGACAACCCT          1483

ATTAATCATT TGGTCTTCTA AAATGGGATC ATGCCCATTT AGATTTCCT TACTATCAGT          1543

TTATTTTTAT AACATTAACT TTTACTTGT TATTTATTAT TTTATATAAT GGTGAGTTTT          1603

TAAATTA                                                                   1610
```

( 2 ) INFORMATION FOR SEQ ID NO:2:

( i ) SEQUENCE CHARACTERISTICS:
        ( A ) LENGTH: 415 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Glu Asp Leu Cys Val Ala Asn Thr Leu Phe Ala Leu Asn Leu Phe
 1               5                  10                 15

Lys His Leu Ala Lys Ala Ser Pro Thr Gln Asn Leu Phe Leu Ser Pro
                20                  25                 30

Trp Ser Ile Ser Ser Thr Met Ala Met Val Tyr Met Gly Ser Arg Gly
            35                  40                 45

Ser Thr Glu Asp Gln Met Ala Lys Val Leu Gln Phe Asn Glu Val Gly
    50                  55                  60

Ala Asn Ala Val Thr Pro Met Thr Pro Glu Asn Phe Thr Ser Cys Gly
65                  70                  75                  80

Phe Met Gln Gln Ile Gln Lys Gly Ser Tyr Pro Asp Ala Ile Leu Gln
                85                  90                  95

Ala Gln Ala Ala Asp Lys Ile His Ser Ser Phe Arg Ser Leu Ser Ser
            100                 105                110

Ala Ile Asn Ala Ser Thr Gly Asn Tyr Leu Leu Glu Ser Val Asn Lys
        115                 120                 125

Leu Phe Gly Glu Lys Ser Ala Ser Phe Arg Glu Glu Tyr Ile Arg Leu
    130                 135                 140

Cys Gln Lys Tyr Tyr Ser Ser Glu Pro Gln Ala Val Asp Phe Leu Glu
145                 150                 155                 160

Cys Ala Glu Glu Ala Arg Lys Lys Ile Asn Ser Trp Val Lys Thr Gln
                165                 170                 175

Thr Lys Gly Lys Ile Pro Asn Leu Leu Pro Glu Gly Ser Val Asp Gly
            180                 185                 190

Asp Thr Arg Met Val Leu Val Asn Ala Val Tyr Phe Lys Gly Lys Trp
        195                 200                 205

Lys Thr Pro Phe Glu Lys Lys Leu Asn Gly Leu Tyr Pro Phe Arg Val
    210                 215                 220

Asn Ser Ala Gln Arg Thr Pro Val Gln Met Met Tyr Leu Arg Glu Lys
225                 230                 235                 240

Leu Asn Ile Gly Tyr Ile Glu Asp Leu Lys Ala Gln Ile Leu Glu Leu
                245                 250                 255

Pro Tyr Ala Gly Asp Val Ser Met Phe Leu Leu Leu Pro Asp Glu Ile
            260                 265                 270
```

| Ala | Asp | Val 275 | Ser | Thr | Gly | Leu | Glu 280 | Leu | Leu | Glu | Ser | Glu 285 | Ile | Thr | Tyr |
| Asp | Lys 290 | Leu | Asn | Lys | Trp | Thr 295 | Ser | Lys | Asp | Lys | Met 300 | Ala | Glu | Asp | Glu |
| Val 305 | Glu | Val | Tyr | Ile | Pro 310 | Gln | Phe | Lys | Leu | Glu 315 | Glu | His | Tyr | Glu | Leu 320 |
| Arg | Ser | Ile | Leu | Arg 325 | Ser | Met | Gly | Met | Glu 330 | Asp | Ala | Phe | Asn | Lys 335 | Gly |
| Arg | Ala | Asn | Phe 340 | Ser | Gly | Met | Ser | Glu 345 | Arg | Asn | Asp | Leu | Phe 350 | Leu | Ser |
| Glu | Val | Phe 355 | His | Gln | Ala | Met | Val 360 | Asp | Val | Asn | Glu | Glu 365 | Gly | Thr | Glu |
| Ala | Ala 370 | Ala | Gly | Thr | Gly | Gly 375 | Val | Met | Thr | Gly | Arg 380 | Thr | Gly | His | Gly |
| Gly 385 | Pro | Gln | Phe | Val | Ala 390 | Asp | His | Pro | Phe | Leu 395 | Phe | Leu | Ile | Met | His 400 |
| Lys | Ile | Thr | Asn | Cys 405 | Ile | Leu | Phe | Phe | Gly 410 | Arg | Phe | Ser | Ser | Pro 415 | |

(2) INFORMATION FOR SEQ ID NO:3:

(i) SEQUENCE CHARACTERISTICS:
        (A) LENGTH: 1512 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (A) ORGANISM: Homo sapiens
        (G) CELL TYPE: Monocyte
        (H) CELL LINE: U937

(vii) IMMEDIATE SOURCE:
        (B) CLONE: BTA 1916

(ix) FEATURE:
        (A) NAME/KEY: CDS
        (B) LOCATION: 22..1200
        (C) IDENTIFICATION METHOD: experimental
        (D) OTHER INFORMATION: /function="Product binds to urokinase, tissue plasminogen activator"
        / product="PAI-2 variant, protease sensitive site removed"
        / evidence=EXPERIMENTAL
        / note="Codes for human plasminogen activator inhibitor type 2 protein in which amino acids 74 to 96 inclusive have been deleted."

(xi) SEQUENCE DESCRIPTION: SEQ ID NO:3:

| GATCTGTAAG | GAGGTATATA | A ATG | GAG | GAT | CTT | TGT | GTG | GCA | AAC | ACA | CTC | 51 |
| | | Met 1 | Glu | Asp | Leu | Cys 5 | Val | Ala | Asn | Thr | Leu 10 | |
| TTT | GCC | CTC | AAT | TTA | TTC | AAG | CAT | CTG | GCA | AAA | GCA | AGC | CCC | ACC | CAG | 99 |
| Phe | Ala | Leu | Asn | Leu 15 | Phe | Lys | His | Leu | Ala 20 | Lys | Ala | Ser | Pro | Thr 25 | Gln | |
| AAC | CTC | TTC | CTC | TCC | CCA | TGG | AGC | ATC | TCG | TCC | ACC | ATG | GCC | ATG | GTC | 147 |
| Asn | Leu | Phe | Leu | Ser 30 | Pro | Trp | Ser | Ile | Ser 35 | Ser | Thr | Met | Ala | Met 40 | Val | |
| TAC | ATG | GGC | TCC | AGG | GGC | AGC | ACC | GAA | GAC | CAG | ATG | GCC | AAG | GTG | CTT | 195 |
| Tyr | Met | Gly 45 | Ser | Arg | Gly | Ser | Thr 50 | Glu | Asp | Gln | Met | Ala 55 | Lys | Val | Leu | |

| | | | | | | | | | | | | | | | | |
|---|---|---|---|---|---|---|---|---|---|---|---|---|---|---|---|---|
| CAG | TTT | AAT | GAA | GTG | GGA | GCC | AAT | GCA | GTT | ACC | CCC | ATG | ACT | CCA | GCA | 243 |
| Gln | Phe | Asn | Glu | Val | Gly | Ala | Asn | Ala | Val | Thr | Pro | Met | Thr | Pro | Ala | |
| | 60 | | | | 65 | | | | | 70 | | | | | | |
| CAA | GCT | GCA | GAT | AAA | ATC | CAT | TCA | TCC | TTC | CGC | TCT | CTC | AGC | TCT | GCA | 291 |
| Gln | Ala | Ala | Asp | Lys | Ile | His | Ser | Ser | Phe | Arg | Ser | Leu | Ser | Ser | Ala | |
| 75 | | | | | 80 | | | | | 85 | | | | | 90 | |
| ATC | AAT | GCA | TCC | ACA | GGG | AAT | TAT | TTA | CTG | GAA | AGT | GTC | AAT | AAG | CTG | 339 |
| Ile | Asn | Ala | Ser | Thr | Gly | Asn | Tyr | Leu | Leu | Glu | Ser | Val | Asn | Lys | Leu | |
| | | | | 95 | | | | | 100 | | | | | 105 | | |
| TTT | GGT | GAG | AAG | TCT | GCG | AGC | TTC | CGG | GAA | GAA | TAT | ATT | CGA | CTC | TGT | 387 |
| Phe | Gly | Glu | Lys | Ser | Ala | Ser | Phe | Arg | Glu | Glu | Tyr | Ile | Arg | Leu | Cys | |
| | | | 110 | | | | | 115 | | | | | 120 | | | |
| CAG | AAA | TAT | TAC | TCC | TCA | GAA | CCC | CAG | GCA | GTA | GAC | TTC | CTA | GAA | TGT | 435 |
| Gln | Lys | Tyr | Tyr | Ser | Ser | Glu | Pro | Gln | Ala | Val | Asp | Phe | Leu | Glu | Cys | |
| | | | 125 | | | | | 130 | | | | | 135 | | | |
| GCA | GAA | GAA | GCT | AGA | AAA | AAG | ATT | AAT | TCC | TGG | GTC | AAG | ACT | CAA | ACC | 483 |
| Ala | Glu | Glu | Ala | Arg | Lys | Lys | Ile | Asn | Ser | Trp | Val | Lys | Thr | Gln | Thr | |
| 140 | | | | | 145 | | | | | 150 | | | | | | |
| AAA | GGC | AAA | ATC | CCA | AAC | TTG | TTA | CCT | GAA | GGT | TCT | GTA | GAT | GGG | GAT | 531 |
| Lys | Gly | Lys | Ile | Pro | Asn | Leu | Leu | Pro | Glu | Gly | Ser | Val | Asp | Gly | Asp | |
| 155 | | | | | 160 | | | | | 165 | | | | | 170 | |
| ACC | AGG | ATG | GTC | CTG | GTG | AAT | GCT | GTC | TAC | TTC | AAA | GGA | AAG | TGG | AAA | 579 |
| Thr | Arg | Met | Val | Leu | Val | Asn | Ala | Val | Tyr | Phe | Lys | Gly | Lys | Trp | Lys | |
| | | | | 175 | | | | | 180 | | | | | 185 | | |
| ACT | CCA | TTT | GAG | AAG | AAA | CTA | AAT | GGG | CTT | TAT | CCT | TTC | CGT | GTA | AAC | 627 |
| Thr | Pro | Phe | Glu | Lys | Lys | Leu | Asn | Gly | Leu | Tyr | Pro | Phe | Arg | Val | Asn | |
| | | | 190 | | | | | 195 | | | | | 200 | | | |
| TCG | GCT | CAG | CGC | ACA | CCT | GTA | CAG | ATG | ATG | TAC | TTG | CGT | GAA | AAG | CTA | 675 |
| Ser | Ala | Gln | Arg | Thr | Pro | Val | Gln | Met | Met | Tyr | Leu | Arg | Glu | Lys | Leu | |
| | | 205 | | | | | 210 | | | | | 215 | | | | |
| AAC | ATT | GGA | TAC | ATA | GAA | GAC | CTA | AAG | GCT | CAG | ATT | CTA | GAA | CTC | CCA | 723 |
| Asn | Ile | Gly | Tyr | Ile | Glu | Asp | Leu | Lys | Ala | Gln | Ile | Leu | Glu | Leu | Pro | |
| | 220 | | | | | 225 | | | | | 230 | | | | | |
| TAT | GCT | GGA | GAT | GTT | AGC | ATG | TTC | TTG | TTG | CTT | CCA | GAT | GAA | ATT | GCC | 771 |
| Tyr | Ala | Gly | Asp | Val | Ser | Met | Phe | Leu | Leu | Leu | Pro | Asp | Glu | Ile | Ala | |
| 235 | | | | | 240 | | | | | 245 | | | | | 250 | |
| GAT | GTG | TCC | ACT | GGC | TTG | GAG | CTG | CTG | GAA | AGT | GAA | ATA | ACC | TAT | GAC | 819 |
| Asp | Val | Ser | Thr | Gly | Leu | Glu | Leu | Leu | Glu | Ser | Glu | Ile | Thr | Tyr | Asp | |
| | | | | 255 | | | | | 260 | | | | | 265 | | |
| AAA | CTC | AAC | AAG | TGG | ACC | AGC | AAA | GAC | AAA | ATG | GCT | GAA | GAT | GAA | GTT | 867 |
| Lys | Leu | Asn | Lys | Trp | Thr | Ser | Lys | Asp | Lys | Met | Ala | Glu | Asp | Glu | Val | |
| | | | 270 | | | | | 275 | | | | | 280 | | | |
| GAG | GTA | TAC | ATA | CCC | CAG | TTC | AAA | TTA | GAA | GAG | CAT | TAT | GAA | CTC | AGA | 915 |
| Glu | Val | Tyr | Ile | Pro | Gln | Phe | Lys | Leu | Glu | Glu | His | Tyr | Glu | Leu | Arg | |
| | | 285 | | | | | 290 | | | | | 295 | | | | |
| TCC | ATT | CTG | AGA | AGC | ATG | GGC | ATG | GAG | GAC | GCC | TTC | AAC | AAG | GGA | CGG | 963 |
| Ser | Ile | Leu | Arg | Ser | Met | Gly | Met | Glu | Asp | Ala | Phe | Asn | Lys | Gly | Arg | |
| | 300 | | | | | 305 | | | | | 310 | | | | | |
| GCC | AAT | TTC | TCA | GGG | ATG | TCG | GAG | AGG | AAT | GAC | CTG | TTT | CTT | TCT | GAA | 1011 |
| Ala | Asn | Phe | Ser | Gly | Met | Ser | Glu | Arg | Asn | Asp | Leu | Phe | Leu | Ser | Glu | |
| 315 | | | | | 320 | | | | | 325 | | | | | 330 | |
| GTG | TTC | CAC | CAA | GCC | ATG | GTG | GAT | GTG | AAT | GAG | GAG | GGC | ACT | GAA | GCA | 1059 |
| Val | Phe | His | Gln | Ala | Met | Val | Asp | Val | Asn | Glu | Glu | Gly | Thr | Glu | Ala | |
| | | | | 335 | | | | | 340 | | | | | 345 | | |
| GCC | GCT | GGC | ACA | GGA | GGT | GTT | ATG | ACA | GGG | AGA | ACT | GGA | CAT | GGA | GGC | 1107 |
| Ala | Ala | Gly | Thr | Gly | Gly | Val | Met | Thr | Gly | Arg | Thr | Gly | His | Gly | Gly | |
| | | | 350 | | | | | 355 | | | | | 360 | | | |
| CCA | CAG | TTT | GTG | GCA | GAT | CAT | CCT | TTT | CTT | TTT | CTT | ATT | ATG | CAT | AAG | 1155 |
| Pro | Gln | Phe | Val | Ala | Asp | His | Pro | Phe | Leu | Phe | Leu | Ile | Met | His | Lys | |
| | | 365 | | | | | 370 | | | | | 375 | | | | |
| ATA | ACC | AAC | TGC | ATT | TTA | TTT | TTC | GGC | AGA | TTT | TCC | TCA | CCC | TAAAACTAAG | | 1207 |
| Ile | Thr | Asn | Cys | Ile | Leu | Phe | Phe | Gly | Arg | Phe | Ser | Ser | Pro | | | |

5,444,153

31 32

-continued

| | | | 380 | | | 385 | | | 390 | | |
|---|---|---|---|---|---|---|---|---|---|---|---|
| CGTGCTGCTT | CTGCAAAAGA | TTTTTGTAGA | TGAGCTGTGT | GCCTCAGAAT | TGCTATTTCA | 1267 |
| AATTGCCAAA | AATTTAGAGA | TGTTTTCTAC | ATATTTCTGC | TCTTCTGAAC | AACTTCTGCT | 1327 |
| ACCCACTAAA | TAAAACACA | GAAATAATTA | GACAATTGTC | TATTATAACA | TGACAACCCT | 1387 |
| ATTAATCATT | TGGTCTTCTA | AAATGGGATC | ATGCCCATTT | AGATTTCCT | TACTATCAGT | 1447 |
| TTATTTTAT | AACATTAACT | TTACTTTGT | TATTTATTAT | TTTATATAAT | GGTGAGTTTT | 1507 |
| TGGGG | | | | | | 1512 |

( 2 ) INFORMATION FOR SEQ ID NO:4:

( i ) SEQUENCE CHARACTERISTICS:
        ( A ) LENGTH: 392 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Met Glu Asp Leu Cys Val Ala Asn Thr Leu Phe Ala Leu Asn Leu Phe
 1               5                  10                  15

Lys His Leu Ala Lys Ala Ser Pro Thr Gln Asn Leu Phe Leu Ser Pro
             20                  25                  30

Trp Ser Ile Ser Ser Thr Met Ala Met Val Tyr Met Gly Ser Arg Gly
         35                  40                  45

Ser Thr Glu Asp Gln Met Ala Lys Val Leu Gln Phe Asn Glu Val Gly
     50                  55                  60

Ala Asn Ala Val Thr Pro Met Thr Pro Ala Gln Ala Ala Asp Lys Ile
 65                  70                  75                  80

His Ser Ser Phe Arg Ser Leu Ser Ser Ala Ile Asn Ala Ser Thr Gly
                 85                  90                  95

Asn Tyr Leu Leu Glu Ser Val Asn Lys Leu Phe Gly Glu Lys Ser Ala
            100                 105                 110

Ser Phe Arg Glu Glu Tyr Ile Arg Leu Cys Gln Lys Tyr Ser Ser
        115                 120                 125

Glu Pro Gln Ala Val Asp Phe Leu Glu Cys Ala Glu Glu Ala Arg Lys
    130                 135                 140

Lys Ile Asn Ser Trp Val Lys Thr Gln Thr Lys Gly Lys Ile Pro Asn
145                 150                 155                 160

Leu Leu Pro Glu Gly Ser Val Asp Gly Asp Thr Arg Met Val Leu Val
                165                 170                 175

Asn Ala Val Tyr Phe Lys Gly Lys Trp Lys Thr Pro Phe Glu Lys Lys
            180                 185                 190

Leu Asn Gly Leu Tyr Pro Phe Arg Val Asn Ser Ala Gln Arg Thr Pro
        195                 200                 205

Val Gln Met Met Tyr Leu Arg Glu Lys Leu Asn Ile Gly Tyr Ile Glu
    210                 215                 220

Asp Leu Lys Ala Gln Ile Leu Glu Leu Pro Tyr Ala Gly Asp Val Ser
225                 230                 235                 240

Met Phe Leu Leu Leu Pro Asp Glu Ile Ala Asp Val Ser Thr Gly Leu
                245                 250                 255

Glu Leu Leu Glu Ser Glu Ile Thr Tyr Asp Lys Leu Asn Lys Trp Thr
            260                 265                 270

Ser Lys Asp Lys Met Ala Glu Asp Glu Val Glu Val Tyr Ile Pro Gln
        275                 280                 285

Phe Lys Leu Glu Glu His Tyr Glu Leu Arg Ser Ile Leu Arg Ser Met
    290                 295                 300
```

```
Gly  Met  Glu  Asp  Ala  Phe  Asn  Lys  Gly  Arg  Ala  Asn  Phe  Ser  Gly  Met
305                      310                      315                      320

Ser  Glu  Arg  Asn  Asp  Leu  Phe  Leu  Ser  Glu  Val  Phe  His  Gln  Ala  Met
                    325                      330                      335

Val  Asp  Val  Asn  Glu  Glu  Gly  Thr  Glu  Ala  Ala  Ala  Gly  Thr  Gly  Gly
               340                      345                      350

Val  Met  Thr  Gly  Arg  Thr  Gly  His  Gly  Gly  Pro  Gln  Phe  Val  Ala  Asp
          355                      360                      365

His  Pro  Phe  Leu  Phe  Leu  Ile  Met  His  Lys  Ile  Thr  Asn  Cys  Ile  Leu
     370                      375                      380

Phe  Phe  Gly  Arg  Phe  Ser  Ser  Pro
385                      390
```

(2) INFORMATION FOR SEQ ID NO:5:

(i) SEQUENCE CHARACTERISTICS:
        (A) LENGTH: 1482 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (A) ORGANISM: Homo sapiens
        (G) CELL TYPE: Monocyte
        (H) CELL LINE: U937

(vii) IMMEDIATE SOURCE:
        (B) CLONE: BTA 1922

(ix) FEATURE:
        (A) NAME/KEY: CDS
        (B) LOCATION: 22..1170
        (C) IDENTIFICATION METHOD: experimental
        (D) OTHER INFORMATION: /function="Product binds to urokinase, tissue plasminogen activator"
        / product="PAI-2 variant, protease sensitive site removed"
        / evidence=EXPERIMENTAL
        / note="Codes for human plasminogen activator inhibitor type 2 protein in which amino acids 66 to 98 inclusive have been deleted."

(xi) SEQUENCE DESCRIPTION: SEQ ID NO:5:

```
GATCTGTAAG  GAGGTATATA  A  ATG  GAG  GAT  CTT  TGT  GTG  GCA  AAC  ACA  CTC         51
                           Met  Glu  Asp  Leu  Cys  Val  Ala  Asn  Thr  Leu
                           1                  5                        10

TTT  GCC  CTC  AAT  TTA  TTC  AAG  CAT  CTG  GCA  AAA  GCA  AGC  CCC  ACC  CAG      99
Phe  Ala  Leu  Asn  Leu  Phe  Lys  His  Leu  Ala  Lys  Ala  Ser  Pro  Thr  Gln
               15                       20                       25

AAC  CTC  TTC  CTC  TCC  CCA  TGG  AGC  ATC  TCG  TCC  ACC  ATG  GCC  ATG  GTC     147
Asn  Leu  Phe  Leu  Ser  Pro  Trp  Ser  Ile  Ser  Ser  Thr  Met  Ala  Met  Val
               30                       35                       40

TAC  ATG  GGC  TCC  AGG  GGC  AGC  ACC  GAA  GAC  CAG  ATG  GCC  AAG  GTG  CTT     195
Tyr  Met  Gly  Ser  Arg  Gly  Ser  Thr  Glu  Asp  Gln  Met  Ala  Lys  Val  Leu
          45                       50                       55

CAG  TTT  AAT  GAA  GTG  GGA  GCC  GCT  GCA  GAT  AAA  ATC  CAT  TCA  TCC  TTC     243
Gln  Phe  Asn  Glu  Val  Gly  Ala  Ala  Ala  Asp  Lys  Ile  His  Ser  Ser  Phe
     60                       65                       70

CGC  TCT  CTC  AGC  TCT  GCA  ATC  AAT  GCA  TCC  ACA  GGG  AAT  TAT  TTA  CTG     291
Arg  Ser  Leu  Ser  Ser  Ala  Ile  Asn  Ala  Ser  Thr  Gly  Asn  Tyr  Leu  Leu
75                       80                       85                       90
```

| | | | | | | | | | | | | | | | | |
|---|---|---|---|---|---|---|---|---|---|---|---|---|---|---|---|---|
| GAA | AGT | GTC | AAT | AAG | CTG | TTT | GGT | GAG | AAG | TCT | GCG | AGC | TTC | CGG | GAA | 339 |
| Glu | Ser | Val | Asn | Lys | Leu | Phe | Gly | Glu | Lys | Ser | Ala | Ser | Phe | Arg | Glu | |
| | | | | 95 | | | | 100 | | | | | 105 | | | |
| GAA | TAT | ATT | CGA | CTC | TGT | CAG | AAA | TAT | TAC | TCC | TCA | GAA | CCC | CAG | GCA | 387 |
| Glu | Tyr | Ile | Arg | Leu | Cys | Gln | Lys | Tyr | Tyr | Ser | Ser | Glu | Pro | Gln | Ala | |
| | | | 110 | | | | 115 | | | | | 120 | | | | |
| GTA | GAC | TTC | CTA | GAA | TGT | GCA | GAA | GAA | GCT | AGA | AAA | AAG | ATT | AAT | TCC | 435 |
| Val | Asp | Phe | Leu | Glu | Cys | Ala | Glu | Glu | Ala | Arg | Lys | Lys | Ile | Asn | Ser | |
| | | 125 | | | | | 130 | | | | | 135 | | | | |
| TGG | GTC | AAG | ACT | CAA | ACC | AAA | GGC | AAA | ATC | CCA | AAC | TTG | TTA | CCT | GAA | 483 |
| Trp | Val | Lys | Thr | Gln | Thr | Lys | Gly | Lys | Ile | Pro | Asn | Leu | Leu | Pro | Glu | |
| | 140 | | | | | 145 | | | | | 150 | | | | | |
| GGT | TCT | GTA | GAT | GGG | GAT | ACC | AGG | ATG | GTC | CTG | GTG | AAT | GCT | GTC | TAC | 531 |
| Gly | Ser | Val | Asp | Gly | Asp | Thr | Arg | Met | Val | Leu | Val | Asn | Ala | Val | Tyr | |
| 155 | | | | | 160 | | | | | 165 | | | | | 170 | |
| TTC | AAA | GGA | AAG | TGG | AAA | ACT | CCA | TTT | GAG | AAG | AAA | CTA | AAT | GGG | CTT | 579 |
| Phe | Lys | Gly | Lys | Trp | Lys | Thr | Pro | Phe | Glu | Lys | Lys | Leu | Asn | Gly | Leu | |
| | | | | 175 | | | | | 180 | | | | | 185 | | |
| TAT | CCT | TTC | CGT | GTA | AAC | TCG | GCT | CAG | CGC | ACA | CCT | GTA | CAG | ATG | ATG | 627 |
| Tyr | Pro | Phe | Arg | Val | Asn | Ser | Ala | Gln | Arg | Thr | Pro | Val | Gln | Met | Met | |
| | | | 190 | | | | | 195 | | | | | 200 | | | |
| TAC | TTG | CGT | GAA | AAG | CTA | AAC | ATT | GGA | TAC | ATA | GAA | GAC | CTA | AAG | GCT | 675 |
| Tyr | Leu | Arg | Glu | Lys | Leu | Asn | Ile | Gly | Tyr | Ile | Glu | Asp | Leu | Lys | Ala | |
| | | 205 | | | | | 210 | | | | | 215 | | | | |
| CAG | ATT | CTA | GAA | CTC | CCA | TAT | GCT | GGA | GAT | GTT | AGC | ATG | TTC | TTG | TTG | 723 |
| Gln | Ile | Leu | Glu | Leu | Pro | Tyr | Ala | Gly | Asp | Val | Ser | Met | Phe | Leu | Leu | |
| | 220 | | | | | 225 | | | | | 230 | | | | | |
| CTT | CCA | GAT | GAA | ATT | GCC | GAT | GTG | TCC | ACT | GGC | TTG | GAG | CTG | CTG | GAA | 771 |
| Leu | Pro | Asp | Glu | Ile | Ala | Asp | Val | Ser | Thr | Gly | Leu | Glu | Leu | Leu | Glu | |
| 235 | | | | | 240 | | | | | 245 | | | | | 250 | |
| AGT | GAA | ATA | ACC | TAT | GAC | AAA | CTC | AAC | AAG | TGG | ACC | AGC | AAA | GAC | AAA | 819 |
| Ser | Glu | Ile | Thr | Tyr | Asp | Lys | Leu | Asn | Lys | Trp | Thr | Ser | Lys | Asp | Lys | |
| | | | | 255 | | | | | 260 | | | | | 265 | | |
| ATG | GCT | GAA | GAT | GAA | GTT | GAG | GTA | TAC | ATA | CCC | CAG | TTC | AAA | TTA | GAA | 867 |
| Met | Ala | Glu | Asp | Glu | Val | Glu | Val | Tyr | Ile | Pro | Gln | Phe | Lys | Leu | Glu | |
| | | | 270 | | | | | 275 | | | | | 280 | | | |
| GAG | CAT | TAT | GAA | CTC | AGA | TCC | ATT | CTG | AGA | AGC | ATG | GGC | ATG | GAG | GAC | 915 |
| Glu | His | Tyr | Glu | Leu | Arg | Ser | Ile | Leu | Arg | Ser | Met | Gly | Met | Glu | Asp | |
| | | 285 | | | | | 290 | | | | | 295 | | | | |
| GCC | TTC | AAC | AAG | GGA | CGG | GCC | AAT | TTC | TCA | GGG | ATG | TCG | GAG | AGG | AAT | 963 |
| Ala | Phe | Asn | Lys | Gly | Arg | Ala | Asn | Phe | Ser | Gly | Met | Ser | Glu | Arg | Asn | |
| | 300 | | | | | 305 | | | | | 310 | | | | | |
| GAC | CTG | TTT | CTT | TCT | GAA | GTG | TTC | CAC | CAA | GCC | ATG | GTG | GAT | GTG | AAT | 1011 |
| Asp | Leu | Phe | Leu | Ser | Glu | Val | Phe | His | Gln | Ala | Met | Val | Asp | Val | Asn | |
| 315 | | | | | 320 | | | | | 325 | | | | | 330 | |
| GAG | GAG | GGC | ACT | GAA | GCA | GCC | GCT | GGC | ACA | GGA | GGT | GTT | ATG | ACA | GGG | 1059 |
| Glu | Glu | Gly | Thr | Glu | Ala | Ala | Ala | Gly | Thr | Gly | Gly | Val | Met | Thr | Gly | |
| | | | | 335 | | | | | 340 | | | | | 345 | | |
| AGA | ACT | GGA | CAT | GGA | GGC | CCA | CAG | TTT | GTG | GCA | GAT | CAT | CCT | TTT | CTT | 1107 |
| Arg | Thr | Gly | His | Gly | Gly | Pro | Gln | Phe | Val | Ala | Asp | His | Pro | Phe | Leu | |
| | | | 350 | | | | | 355 | | | | | 360 | | | |
| TTT | CTT | ATT | ATG | CAT | AAG | ATA | ACC | AAC | TGC | ATT | TTA | TTT | TTC | GGC | AGA | 1155 |
| Phe | Leu | Ile | Met | His | Lys | Ile | Thr | Asn | Cys | Ile | Leu | Phe | Phe | Gly | Arg | |
| | | | 365 | | | | 370 | | | | | 375 | | | | |
| TTT | TCC | TCA | CCC | TAAAACTAAG | CGTGCTGCTT | CTGCAAAAGA | TTTTTGTAGA | | | | | | | | | 1207 |
| Phe | Ser | Ser | Pro | | | | | | | | | | | | | |
| | 380 | | | | | | | | | | | | | | | |

TGAGCTGTGT GCCTCAGAAT TGCTATTTCA AATTGCCAAA AATTTAGAGA TGTTTTCTAC    1267

ATATTTCTGC TCTTCTGAAC AACTTCTGCT ACCCACTAAA TAAAACACA GAAATAATTA    1327

GACAATTGTC TATTATAACA TGACAACCCT ATTAATCATT TGGTCTTCTA AAATGGGATC    1387

```
ATGCCCATTT AGATTTTCCT TACTATCAGT TTATTTTTAT AACATTAACT TTTACTTTGT     1447

TATTTATTAT TTTATATAAT GGTGAGTTTT TGGGG                                1482
```

( 2 ) INFORMATION FOR SEQ ID NO:6:

( i ) SEQUENCE CHARACTERISTICS:
        ( A ) LENGTH: 382 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

```
Met  Glu  Asp  Leu  Cys  Val  Ala  Asn  Thr  Leu  Phe  Ala  Leu  Asn  Leu  Phe
 1              5                        10                       15

Lys  His  Leu  Ala  Lys  Ala  Ser  Pro  Thr  Gln  Asn  Leu  Phe  Leu  Ser  Pro
           20                       25                       30

Trp  Ser  Ile  Ser  Ser  Thr  Met  Ala  Met  Val  Tyr  Met  Gly  Ser  Arg  Gly
          35                   40                       45

Ser  Thr  Glu  Asp  Gln  Met  Ala  Lys  Val  Leu  Gln  Phe  Asn  Glu  Val  Gly
      50                 55                       60

Ala  Ala  Ala  Asp  Lys  Ile  His  Ser  Ser  Phe  Arg  Ser  Leu  Ser  Ser  Ala
 65                       70                       75                       80

Ile  Asn  Ala  Ser  Thr  Gly  Asn  Tyr  Leu  Leu  Glu  Ser  Val  Asn  Lys  Leu
                 85                       90                       95

Phe  Gly  Glu  Lys  Ser  Ala  Ser  Phe  Arg  Glu  Glu  Tyr  Ile  Arg  Leu  Cys
               100                      105                      110

Gln  Lys  Tyr  Tyr  Ser  Ser  Glu  Pro  Gln  Ala  Val  Asp  Phe  Leu  Glu  Cys
          115                      120                      125

Ala  Glu  Glu  Ala  Arg  Lys  Lys  Ile  Asn  Ser  Trp  Val  Lys  Thr  Gln  Thr
     130                      135                      140

Lys  Gly  Lys  Ile  Pro  Asn  Leu  Leu  Pro  Glu  Gly  Ser  Val  Asp  Gly  Asp
145                      150                      155                      160

Thr  Arg  Met  Val  Leu  Val  Asn  Ala  Val  Tyr  Phe  Lys  Gly  Lys  Trp  Lys
                165                      170                      175

Thr  Pro  Phe  Glu  Lys  Lys  Leu  Asn  Gly  Leu  Tyr  Pro  Phe  Arg  Val  Asn
               180                      185                      190

Ser  Ala  Gln  Arg  Thr  Pro  Val  Gln  Met  Met  Tyr  Leu  Arg  Glu  Lys  Leu
          195                      200                      205

Asn  Ile  Gly  Tyr  Ile  Glu  Asp  Leu  Lys  Ala  Gln  Ile  Leu  Glu  Leu  Pro
     210                      215                      220

Tyr  Ala  Gly  Asp  Val  Ser  Met  Phe  Leu  Leu  Leu  Pro  Asp  Glu  Ile  Ala
225                      230                      235                      240

Asp  Val  Ser  Thr  Gly  Leu  Glu  Leu  Leu  Glu  Ser  Glu  Ile  Thr  Tyr  Asp
                245                      250                      255

Lys  Leu  Asn  Lys  Trp  Thr  Ser  Lys  Asp  Lys  Met  Ala  Glu  Asp  Glu  Val
               260                      265                      270

Glu  Val  Tyr  Ile  Pro  Gln  Phe  Lys  Leu  Glu  Glu  His  Tyr  Glu  Leu  Arg
          275                      280                      285

Ser  Ile  Leu  Arg  Ser  Met  Gly  Met  Glu  Asp  Ala  Phe  Asn  Lys  Gly  Arg
     290                      295                      300

Ala  Asn  Phe  Ser  Gly  Met  Ser  Glu  Arg  Asn  Asp  Leu  Phe  Leu  Ser  Glu
305                      310                      315                      320

Val  Phe  His  Gln  Ala  Met  Val  Asp  Val  Asn  Glu  Glu  Gly  Thr  Glu  Ala
                325                      330                      335

Ala  Ala  Gly  Thr  Gly  Gly  Val  Met  Thr  Gly  Arg  Thr  Gly  His  Gly  Gly
               340                      345                      350
```

| Pro | Gln | Phe | Val | Ala | Asp | His | Pro | Phe | Leu | Phe | Leu | Ile | Met | His | Lys |
|-----|-----|-----|-----|-----|-----|-----|-----|-----|-----|-----|-----|-----|-----|-----|-----|
|     | 355 |     |     |     |     |     | 360 |     |     |     |     | 365 |     |     |     |

| Ile | Thr | Asn | Cys | Ile | Leu | Phe | Phe | Gly | Arg | Phe | Ser | Ser | Pro |
|-----|-----|-----|-----|-----|-----|-----|-----|-----|-----|-----|-----|-----|-----|
| 370 |     |     |     |     |     | 375 |     |     |     |     | 380 |     |     |

( 2 ) INFORMATION FOR SEQ ID NO:7:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: Other nucleic acid;
        ( A ) DESCRIPTION: Synthetic DNA oligonucleotide ( i i i ) HYPOTHETICAL: NO ( i v ) ANTI-SENSE: NO ( x i ) SEQUENCE DESCRIPTION: SEQ ID NO:7:

GGCCCATATG ATATCTCGAG ACTAGTC        27

( 2 ) INFORMATION FOR SEQ ID NO:8:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: Other nucleic acid;
        ( A ) DESCRIPTION: Synthetic DNA adaptor for replacing HinfI/Pst
            region of PAI-2 gene in 74-96 amino acid coding
            region deletion variant.

( i i i ) HYPOTHETICAL: NO ( i v ) ANTI-SENSE: NO ( i x ) FEATURE:
        ( A ) NAME/KEY: CDS
        ( B ) LOCATION: 1..18

( x i ) SEQUENCE DESCRIPTION: SEQ ID NO:8:

| ACT | CCA | GCA | CAA | GCT | GCA |     |
|-----|-----|-----|-----|-----|-----|-----|
| Thr | Pro | Ala | Gln | Ala | Ala | 18  |
| 1   |     |     |     | 5   |     |     |

( 2 ) INFORMATION FOR SEQ ID NO:9:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: protein ( x i ) SEQUENCE DESCRIPTION: SEQ ID NO:9:

| Thr | Pro | Ala | Gln | Ala | Ala |
|-----|-----|-----|-----|-----|-----|
| 1   |     |     |     | 5   |     |

( 2 ) INFORMATION FOR SEQ ID NO:10:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear ( i i ) MOLECULE TYPE: Other nucleic acid;
        ( A ) DESCRIPTION: Complementary sequence to SEQ ID NO:8 adaptor
            for replacing HinfI/PstI region of PAI-2 gene in
            74-96 amino acid coding region deletion variant.

( i i i ) HYPOTHETICAL: NO ( i v ) ANTI-SENSE: YES ( x i ) SEQUENCE DESCRIPTION: SEQ ID NO:10:

GCTTGTGCTG G                                                                                     11

( 2 ) INFORMATION FOR SEQ ID NO:11:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: Other nucleic acid;
        ( A ) DESCRIPTION: Synthetic DNA oligonucleotide for use in PCR
            reaction to create gene encoding 66-98 amino
            acid deletion variant of PAI-2.

( i i i ) HYPOTHETICAL: NO ( i v ) ANTI-SENSE: YES ( x i ) SEQUENCE DESCRIPTION: SEQ ID NO:11:

CCTCTTCTGC AGATTCTAGG AA 22

( 2 ) INFORMATION FOR SEQ ID NO:12:

( i ) SEQUENCE CHARACTERISTICS:
( A ) LENGTH: 29 base pairs
( B ) TYPE: nucleic acid
( C ) STRANDEDNESS: single
( D ) TOPOLOGY: linear ( i i ) MOLECULE TYPE: Other nucleic acid;
( A ) DESCRIPTION: Synthetic DNA oligonucleotide for use in PCR reaction to create gene encoding 66-98 amino acid deletion variant of PAI-2.

( i i i ) HYPOTHETICAL: NO ( i v ) ANTI-SENSE: YES ( x i ) SEQUENCE DESCRIPTION: SEQ ID NO:12:

ATCTGCAGCG GCTCCCACTT CATTAAACT 29

( 2 ) INFORMATION FOR SEQ ID NO:13:

( i ) SEQUENCE CHARACTERISTICS:
( A ) LENGTH: 28 base pairs
( B ) TYPE: nucleic acid
( C ) STRANDEDNESS: single
( D ) TOPOLOGY: linear ( i i ) MOLECULE TYPE: Other nucleic acid;
( A ) DESCRIPTION: Synthetic DNA oligonucleotide for use in PCR reaction to create gene encoding 66-98 amnio acid deletion variant of PAI-2.

( i i i ) HYPOTHETICAL: NO ( i v ) ANTI-SENSE: NO ( x i ) SEQUENCE DESCRIPTION: SEQ ID NO:13:

GTGGGAGCCG CTGCAGATAA AATCCATT 28

( 2 ) INFORMATION FOR SEQ ID NO:14:

( i ) SEQUENCE CHARACTERISTICS:
( A ) LENGTH: 27 base pairs
( B ) TYPE: nucleic acid
( C ) STRANDEDNESS: single (D) TOPOLOGY: linear (ii) MOLECULE TYPE: Other nucleic acid;
    (A) DESCRIPTION: Synthetic DNA oligonucleotide (iii) HYPOTHETICAL: NO (iv) ANTI-SENSE: NO (xi) SEQUENCE DESCRIPTION: SEQ ID NO:14:

GATCTNNNNN NNNNNNNNNN NATGGAG      27

(2) INFORMATION FOR SEQ ID NO:15:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: Other nucleic acid;
        (A) DESCRIPTION: Synthetic DNA oligonucleotide (iii) HYPOTHETICAL: NO (iv) ANTI-SENSE: NO (xi) SEQUENCE DESCRIPTION: SEQ ID NO:15:

GATCTNNNNN NNNNNNNNNN ATGGAG      26

(2) INFORMATION FOR SEQ ID NO:16:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:16:

Lys Gly Ser Tyr Pro Asp Ala Ile Leu Gln Ala Gln Ala Ala Asp
1               5                     10                    15

(2) INFORMATION FOR SEQ ID NO:17:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:17:

Phe Met Gln Gln Ile Gln Lys Gly Ser Tyr
1               5                     10

(2) INFORMATION FOR SEQ ID NO:18:

(i) SEQUENCE CHARACTERISTICS:
        (A) LENGTH: 15 amino acids
        (B) TYPE: amino acid
        (D) TOPOLOGY: linear (i i) MOLECULE TYPE: peptide (i i i) HYPOTHETICAL: NO (i v) ANTI-SENSE: NO (v) FRAGMENT TYPE: N-terminal (x i) SEQUENCE DESCRIPTION: SEQ ID NO:18:

```
Gly Phe Met Gln Gln Ile Gln Lys Gly Ser Tyr Pro Asp Ala Ile
 1           5                  10                      15
```

(2) INFORMATION FOR SEQ ID NO:19:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (i i) MOLECULE TYPE: Other nucleic acid;
        (A) DESCRIPTION: Synthetic DNA oligonucleotide (i i i) HYPOTHETICAL: NO (i v) ANTI-SENSE: NO (i x) FEATURE:
        (A) NAME/KEY: CDS
        (B) LOCATION: 1..27

(x i) SEQUENCE DESCRIPTION: SEQ ID NO:19:

```
CAG CAG ATC CAG GCA GGT AGT TAT CCT                    27
Gln Gln Ile Gln Ala Gly Ser Tyr Pro
 1           5
```

(2) INFORMATION FOR SEQ ID NO:20:

(i) SEQUENCE CHARACTERISTICS:
        (A) LENGTH: 9 amino acids
        (B) TYPE: amino acid
        (D) TOPOLOGY: linear (i i) MOLECULE TYPE: protein (x i) SEQUENCE DESCRIPTION: SEQ ID NO:20:

```
Gln Gln Ile Gln Ala Gly Ser Tyr Pro
 1           5
```

(2) INFORMATION FOR SEQ ID NO:21:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (i i) MOLECULE TYPE: Other nucleic acid;
        (A) DESCRIPTION: Synthetic DNA oligonucleotide, complement to
            SEQ ID NO:19.

(i i i) HYPOTHETICAL: NO (i v) ANTI-SENSE: YES (x i) SEQUENCE DESCRIPTION: SEQ ID NO:21:

AGGATAACTA CCTGCCTGGA TCTGCTG                              27

* * * * *